US012390607B2

(12) United States Patent
Cappelli et al.

(10) Patent No.: US 12,390,607 B2
(45) Date of Patent: Aug. 19, 2025

(54) PRESSURE SENSOR EVALUATION FOR RESPIRATORY APPARATUS

(71) Applicant: ResMed Pty Ltd, Bella Vista (AU)

(72) Inventors: Joel Cappelli, Sydney (AU); Cem Tarakci, Sydney (AU); Barton John Kenyon, Sydney (AU)

(73) Assignee: ResMed Pty Ltd (AU)

( * ) Notice: Subject to any disclaimer, the term of this patent is extended or adjusted under 35 U.S.C. 154(b) by 63 days.

(21) Appl. No.: 18/350,955

(22) Filed: Jul. 12, 2023

(65) Prior Publication Data

US 2023/0347083 A1 Nov. 2, 2023

Related U.S. Application Data

(63) Continuation of application No. 16/735,860, filed on Jan. 7, 2020, now Pat. No. 11,730,905, which is a (Continued)

(51) Int. Cl.
*A61M 16/00* (2006.01)
*G01L 27/00* (2006.01)

(52) U.S. Cl.
CPC .... *A61M 16/0003* (2014.02); *A61M 16/0051* (2013.01); *A61M 16/0069* (2014.02);

(Continued)

(58) Field of Classification Search
CPC ............ A61M 16/0003; A61M 16/026; A61M 16/0069; A61M 2016/0027;

(Continued)

(56) References Cited

U.S. PATENT DOCUMENTS 2,465,775 A 3/1949 White
4,263,804 A 4/1981 Seemann (Continued)

FOREIGN PATENT DOCUMENTS

CA 2611603 A1 1/2007
CN 101060878 A 10/2007

(Continued)

OTHER PUBLICATIONS

CN Office Action mailed Aug. 17, 2020 for CN Application No. 201710354050.3.

(Continued)

*Primary Examiner* — Colin W Stuart
*Assistant Examiner* — Douglas Y Sul
(74) *Attorney, Agent, or Firm* — Botos Churchill IP Law LLP

(57) ABSTRACT

A respiratory apparatus evaluates accuracy of a pressure sensor, such as when only a single pressure sensor is provided. The accuracy of the pressure sensor may be assessed based on pressure measurement obtained from the pressure sensor and a subordinate or secondary characteristic of the respiratory device such as altitude or atmospheric pressure. A controller or processor may calculate the altitude of the respiratory device based in part on the pressure measurement. In some embodiments, the assessment of the pressure sensor may involve an evaluation of the calculated altitude. In some cases, the assessment of the pressure sensor may involve determining an estimated pressure based on a calculated altitude, and comparing the pressure measurement obtained from the pressure sensor with the estimated pressure.

52 Claims, 13 Drawing Sheets

Related U.S. Application Data continuation of application No. 14/411,769, filed as application No. PCT/AU2013/000695 on Jun. 27, 2013, now Pat. No. 10,569,035.

(60) Provisional application No. 61/666,367, filed on Jun. 29, 2012.

(52) U.S. Cl.
CPC ......... *A61M 16/026* (2017.08); *G01L 27/007* (2013.01); *A61M 2016/0027* (2013.01); *A61M 2016/003* (2013.01); *A61M 2205/18* (2013.01); *A61M 2205/3365* (2013.01); *A61M 2205/3368* (2013.01); *A61M 2205/502* (2013.01); *A61M 2205/70* (2013.01)

(58) Field of Classification Search
CPC .... A61M 2016/003; A62B 7/14; A62B 9/006; A62B 27/00; G01L 27/005; G01L 27/007
USPC ....................... 73/1.16–1.41, 1.57, 1.59, 384
See application file for complete search history.

(56) References Cited

U.S. PATENT DOCUMENTS

| | | | | |
|---|---|---|---|---|
| 5,199,426 | A | 4/1993 | Aldworth et al. | |
| 5,598,838 | A | 2/1997 | Servidio et al. | |
| 5,603,315 | A | 2/1997 | Sasso | |
| 5,686,664 | A | 11/1997 | Pearcy | |
| 6,220,244 | B1 | 4/2001 | McLaughlin | |
| 6,266,583 | B1 | 7/2001 | Tazartes et al. | |
| 6,349,724 | B1 * | 2/2002 | Burton | A61M 16/0057 128/204.22 |
| 6,701,282 | B2 | 3/2004 | Ting | |
| 6,895,962 | B2 | 5/2005 | Kullik et al. | |
| 7,343,917 | B2 | 3/2008 | Jones | |
| 7,369,757 | B2 | 5/2008 | Farbarik | |
| 7,537,010 | B2 | 5/2009 | Colla et al. | |
| 9,180,266 | B1 | 11/2015 | Sherman | |
| 9,808,656 | B2 | 11/2017 | Vinnakota | |
| 10,569,035 | B2 | 2/2020 | Cappelli et al. | |
| 10,569,038 | B2 | 2/2020 | Hoftman et al. | |
| 2001/0004894 | A1 | 6/2001 | Bourdon | |
| 2003/0136191 | A1 | 7/2003 | Tsuji | |
| 2003/0195682 | A1 | 10/2003 | Lee | |
| 2005/0019164 | A1 | 1/2005 | Delano et al. | |
| 2006/0283450 | A1 | 12/2006 | Shissler | |
| 2008/0302364 | A1 | 12/2008 | Garde | |
| 2009/0199850 | A1 * | 8/2009 | Colla | A61M 16/00 128/204.21 |
| 2009/0254257 | A1 | 10/2009 | Dlugoss | |
| 2009/0266361 | A1 | 10/2009 | Bigler et al. | |
| 2009/0301488 | A1 | 12/2009 | Sun | |
| 2010/0078024 | A1 | 4/2010 | Andrieux | |
| 2010/0292544 | A1 | 11/2010 | Sherman et al. | |
| 2011/0209706 | A1 * | 9/2011 | Truschel | A61M 16/024 128/204.23 |
| 2011/0276254 | A1 | 11/2011 | Tsukamoto | |
| 2012/0138051 | A1 | 6/2012 | Curran et al. | |
| 2013/0174845 | A1 * | 7/2013 | Vinnakota | A62B 9/006 128/204.22 |
| 2015/0020807 | A1 * | 1/2015 | Kimmel | A61M 16/0875 128/204.21 |

FOREIGN PATENT DOCUMENTS

| | | | |
|---|---|---|---|
| CN | 101554872 | A | 10/2009 |
| CN | 102397616 | A | 4/2012 |
| CN | 102470260 | A | 5/2012 |
| GB | 2482216 | A | 1/2012 |
| JP | 2002529154 | A | 9/2002 |
| JP | 2007246240 | A | 9/2007 |
| JP | 2008513114 | A | 5/2008 |
| JP | 2009178428 | A | 8/2009 |
| JP | 2012505688 | A | 3/2012 |
| JP | 2012505689 | | 3/2012 |
| WO | 0027457 | A1 | 5/2000 |
| WO | 2006047826 | A1 | 5/2006 |
| WO | 2010044035 | A1 | 4/2010 |
| WO | 2010044036 | A1 | 4/2010 |
| WO | 2011019778 | A1 | 2/2011 |
| WO | 2011051715 | A2 | 5/2011 |
| WO | 2011071976 | A2 | 6/2011 |
| WO | 2013001425 | A2 | 1/2013 |

OTHER PUBLICATIONS

Extended European Search Report issued in corresponding EP application No. 18159221.3 on Jul. 9, 2018.
International Search Report and Written Opinion for Application No. PCT/AU2013/000695 dated Aug. 23, 2013.
Japanese Office Action mailed Oct. 20, 2017 (English Translation).
JP Notice of Allowance mailed Mar. 3, 2021 for JP Application No. 2019-062988.
"European Search Report for EP13810689.3", Feb. 10, 2016.

* cited by examiner

PRESSURE SENSOR EVALUATION FOR RESPIRATORY APPARATUS

CROSS REFERENCE TO RELATED APPLICATIONS

This application is a continuation of U.S. patent application Ser. No. 16/735,860 filed on Jan. 7, 2020, which is a continuation of U.S. patent application Ser. No. 14/411,769 filed on Dec. 29, 2014, which is a national phase entry under 35 U.S.C. § 371 of International Application No. PCT/AU2013/000695 filed Jun. 27, 2013, published in English, which claims priority from U.S. Provisional Patent Application No. 61/666,367 filed Jun. 29, 2012, all of which are incorporated herein by reference.

FIELD OF TECHNOLOGY

The present technology relates to methods for monitoring accuracy of sensors used for respiratory apparatus, such as methods and apparatus for determining accuracy of a pressure sensor.

BACKGROUND OF THE TECHNOLOGY

Patients diagnosed with disordered breathing problems, such as sleep disordered breathing, snoring, upper airway flow limitation, hypopnea, apnea, or similar, may rely on a respiratory apparatus, such as a continuous positive airway pressure (CPAP) or a BiLevel positive pressure device, to assist with maintaining an open airway. Other forms of a respiratory apparatus include a ventilator. A ventilator assists a patient to breathe by providing oxygen to the lungs and removing carbon dioxide from the body. A ventilator can be used for a patient that is unable to or has a reduced capacity to, for example due to lung disease, breathe on their own.

A respiratory apparatus may include a flow generator coupled to a patient interface (e.g., mask or cannula, etc.) to generate a supply of positively pressurized gas for supply to the patient's airways at one or more pressures.

A respiratory apparatus may also include one or more sensors, such as a pressure sensor, to monitor characteristics of the breathable gas, such as pressure, to be provided to the patient. Based on the measured characteristics, the apparatus may control adjustments to respiratory parameters such as by changing a treatment pressure above atmospheric pressure to splint open an obstructed or partially obstructed patient airway or a change in a pressure support (PS) to provide ventilation that meets a target volume where pressure support is a difference between an inspiratory pressure and an expiratory pressure. Such adjustments may be made by a controller setting or adjusting the motor speed of the flow generator or the controller setting of an aperture of a relief valve of the system. A false reading by any sensor involved in the control of the breathable gas may yield inaccurate control thereof, which, in turn, may adversely affect patient breathing, comfort or safety.

To ensure accurate performance by a respiratory apparatus, it may be desirable to develop methods for monitoring or detecting the accuracy of sensors, before and/or during use, such as a pressure sensor, or for detecting a fault with such sensors.

BRIEF SUMMARY OF THE TECHNOLOGY

Some embodiments of the present technology include a methodology to monitor accuracy of a sensor involved in control of a respiratory treatment.

Some embodiments of the present technology include a respiratory apparatus that monitors accuracy of a sensor involved in its control of the apparatus.

Some embodiments may evaluate a pressure sensor based on a subordinate or secondary characteristic of the apparatus.

Some embodiments may evaluate a pressure sensor based on an altitude of the apparatus.

Some embodiments may evaluate a pressure sensor based on an atmospheric pressure, such as an atmospheric pressure, of the apparatus or in which the apparatus is operated.

Some such embodiments may achieve such monitoring without redundant sensors. For example, some embodiments may evaluate a pressure sensor without an additional pressure sensor. Some embodiments may evaluate a pressure sensor without an altimeter.

Some embodiments of the present technology include a method for determining accuracy of a pressure sensor in a respiratory device. The method may include measuring a pressure of a flow of breathable gas generated by the respiratory device using the pressure sensor. The method may also include determining, with a processor, accuracy of the pressure sensor based on the measured pressure and an altitude of the respiratory device.

In some cases, the respiratory device may include a flow generator with a motor included therein to generate a pressurised flow of breathable gas. The altitude of the respiratory device may be input by a user. The altitude of the respiratory device may be measured by an altimeter of the respiratory device. In some cases, the processor may calculate an estimate of the altitude of the respiratory device. Moreover, the processor may determine the accuracy of the pressure sensor based on an evaluation of the calculated altitude.

In some cases, the processor may calculate the altitude of the respiratory device as a function of (a) the pressure measured by the pressure sensor and one or both of (b)(1) a measured flow rate of the flow of breathable gas and (b)(2) a measured motor speed of the flow generator. Optionally, the processor may calculate the altitude of the respiratory device as a function of a measured temperature of the flow of breathable gas.

The processor may calculate the altitude of the respiratory device when the flow generator controls the gas at a constant predetermined flow rate, such as about 20 liters/minute, or a constant predetermined flow rate that is less than 50 liters/minute, or a constant predetermined flow rate that is in the range between about 10 liters/minute and about 60 liters/minute. Still further, the processor may calculate the altitude of the respiratory device when the flow generator controls a constant predetermined motor speed.

In some cases, the processor may evaluate the calculated altitude by comparing the calculated altitude with a predetermined range of altitudes. In some cases, the predetermined range of altitudes may be between 0 and 9000 feet above sea level. The predetermined range of altitudes may be between 500 feet below sea level and 10,000 feet above sea level. The processor may deem the calculated altitude acceptable when the calculated altitude is within the predetermined range of altitudes. The processor may deem the calculated altitude unacceptable when the calculated altitude is outside the predetermined range of altitudes.

In some cases, the processor may calculate the altitude of the respiratory device at a predetermined frequency over a predetermined period of time. The predetermined frequency may be between about 1 and 2 hertz. The predetermined period of time may be about 5 seconds. Optionally, the processor may evaluate the pressure sensor based on an average of the calculated altitudes. The processor may even determine the pressure sensor to be accurate when an average of the calculated altitudes satisfies a threshold comparison. The processor may evaluate the pressure sensor in an initialization process before the respiratory device provides treatment to a patient. In some cases, the processor may store the altitude of the respiratory device in a memory.

In some versions, the processor may evaluate accuracy of the pressure sensor by calculating expected pressure of the gas generated by the respiratory device and by comparing the measured pressure with the expected pressure. The processor may calculate the expected pressure from the altitude of the respiratory device, a measured flow rate of the flow of breathable gas, and a measured motor speed of the flow generator. The processor may calculate the expected pressure from a measured temperature of the flow of breathable gas. The processor may determine the accuracy of the pressure sensor by comparing a difference between the measured pressure and the expected pressure with a predetermined threshold. The predetermined threshold may be about 5 $cmH_2O$. The processor may determine the pressure sensor inaccurate when the difference exceeds the predetermined threshold. The processor may determine the pressure sensor to be accurate when the difference is within the predetermined threshold. In some cases, the measurement of the pressure, the calculation of the expected pressure, and the comparison of the measured pressure with the expected pressure may be performed at a predetermined frequency over a predetermined period of time. The predetermined frequency may be between about 1 and 2 hertz. The predetermined period of time may be about 5 seconds. In some cases, the processor may determine the pressure sensor to be inaccurate based on a plurality of comparisons between measured pressures and expected pressures.

In some cases, the altitude of the respiratory device may be a first altitude, and the processor may determine the accuracy of the pressure sensor by calculating a second altitude of the respiratory device and by comparing the second altitude of the respiratory device with the first altitude of the respiratory device. The processor may calculate the second altitude of the respiratory device from a measured flow rate of the flow of breathable gas, a measured motor speed of the flow generator, and the pressure measured by the pressure sensor. The processor may calculate the second altitude of the respiratory device from a measured temperature of the flow of breathable gas. The processor may determine the accuracy of the pressure sensor by comparing a difference between the first altitude and the second altitude with a predetermined threshold. The predetermined threshold may be about 600 feet, for example. The processor may determine the pressure sensor to be inaccurate when the difference exceeds the predetermined threshold. The processor may determine the pressure sensor to be accurate when the difference is within the predetermined threshold. The processor may calculate the second altitude at a predetermined frequency for a predetermined period of time. The predetermined frequency may be between about 1 and 2 hertz. The predetermined period of time may be about 5 seconds.

In some such cases, the processor may determine the pressure sensor inaccurate when an average of the second altitude calculated during the predetermined period of time differs from the first altitude by an offset greater than a predetermined threshold. The processor may determine the pressure sensor accurate when an average of the second altitude calculated during the predetermined period of time differs from the first altitude by an offset not greater than a predetermined threshold.

In some versions, the method may include setting a motor speed for the flow generator based on the measured pressure, when the processor determines the pressure sensor inaccurate. The method may also include maintaining the motor speed under a speed limit threshold. The method may also include determining a desired gas pressure to be generated by the flow generator, and determining a desired motor speed for the flow generator based on a predetermined association between motor speed values and pressure values.

Some embodiments of the present technology include a respiratory apparatus. The apparatus may include a flow generator with a blower included therein to generate a breathable gas for a patient interface at a pressure above atmospheric pressure. A pressure sensor may be coupled with the flow generator and may be configured to measure pressure of the flow of breathable gas. The apparatus may also include a processor coupled with the pressure sensor and configured to determine accuracy of the pressure sensor based on the measured pressure and an altitude of the respiratory apparatus.

The respiratory apparatus may also include a flow sensor configured to measure a flow rate of the flow of breathable gas. The respiratory apparatus may also include a motor speed sensor configured to measure a motor speed of the flow generator. The respiratory apparatus may also include a user input/output (I/O) device configured to receive the altitude of the respiratory apparatus input by a user. The respiratory apparatus may also include an altimeter to determine the altitude of the respiratory apparatus.

The processor may be configured to set the flow generator to a motor speed based on the pressure measured by the pressure sensor, when the processor determines the pressure sensor inaccurate. The processor may be configured to maintain the motor speed under a speed limit threshold. The processor may be configured to determine a desired gas pressure to be generated by the flow generator, and to determine a desired motor speed for the flow generator based on a predetermined association between motor speed values and pressure values.

The subject headings used in the detailed description are included only for the ease of reference of the reader and should not be used to limit the subject matter found throughout the disclosure or the claims. The subject headings should not be used in construing the scope of the claims or the claim limitations.

Various aspects of the described example embodiments may be combined with aspects of certain other example embodiments to realize yet further embodiments. It is to be understood that one or more features of any one example may be combinable with one or more features of the other examples. In addition, any single feature or combination of features in any example or examples may constitute patentable subject matter.

Other features of the technology will be apparent from consideration of the information contained in the following detailed description.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
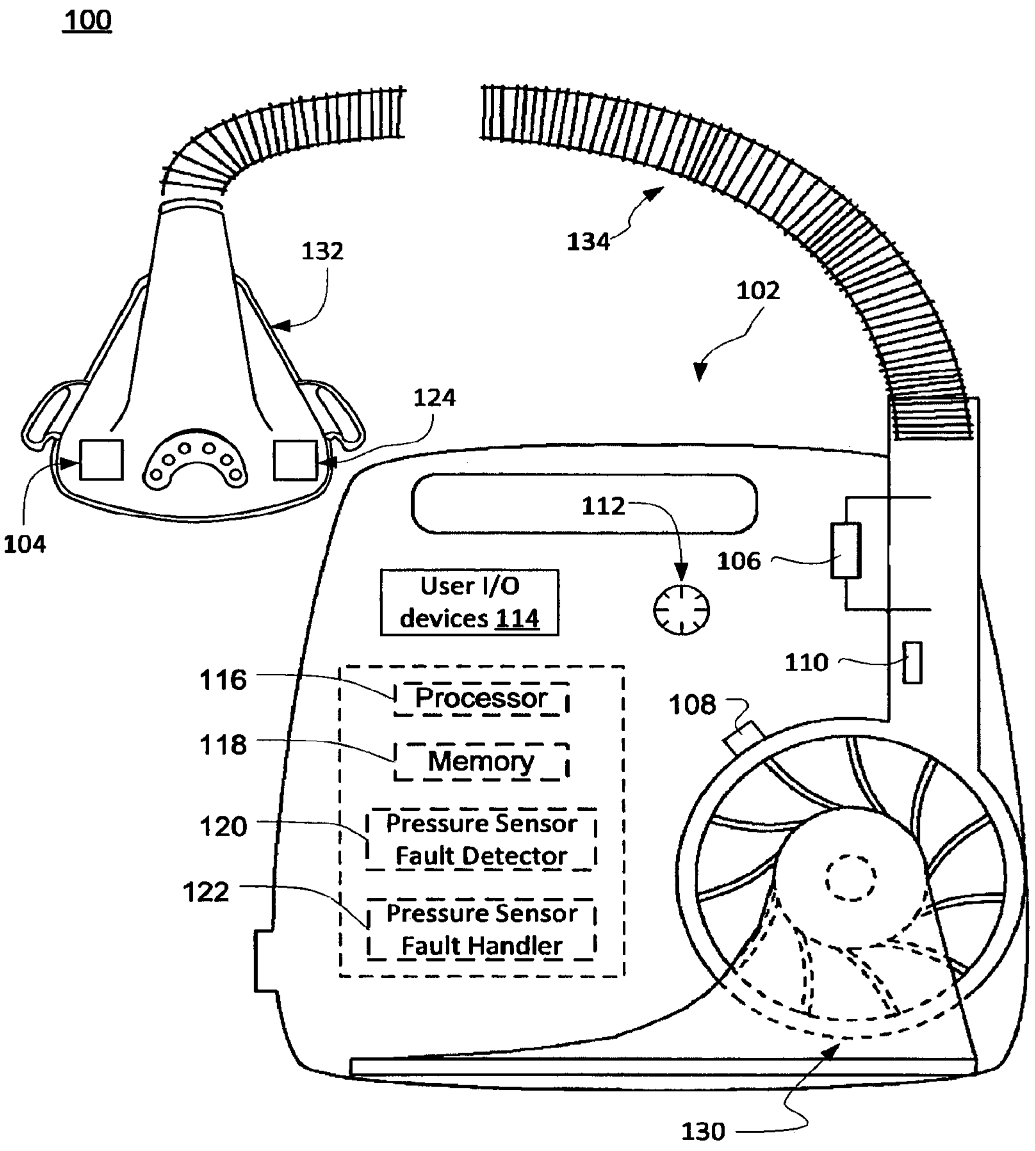
FIG. 1 shows an example respiratory apparatus of the present technology.

For simplicity and clarity of illustration, like reference numerals may be used in the drawings to identify identical or analogous structural elements.

Flow diagrams may be used in the drawings to illustrate processes, operations or methods performed by components, devices, parts, systems, or apparatuses disclosed herein. The flow diagrams are mere exemplary illustrations of steps or algorithms performed in individual processes, operations or methods, such as by a suitably configured controller or processor. The processes may be performed in the precise order as illustrated in the flow diagrams. Alternatively, various steps may be handled simultaneously or performed in sequences different from that illustrated. Steps may also be omitted from or added to the flow diagrams unless otherwise stated.

Example System Components

As illustrated in FIG. 1, example embodiments of the present technology may include a respiratory apparatus 100. The respiratory apparatus 100 may be any type of a respiratory apparatus including, but not limited to: a continuous positive airway pressure (CPAP) device, an automatic positive airway pressure (APAP) device, a bi-level positive airway pressure (BPAP) device, a variable positive airway pressure (VPAP) device, and a ventilator.

Figure 2:
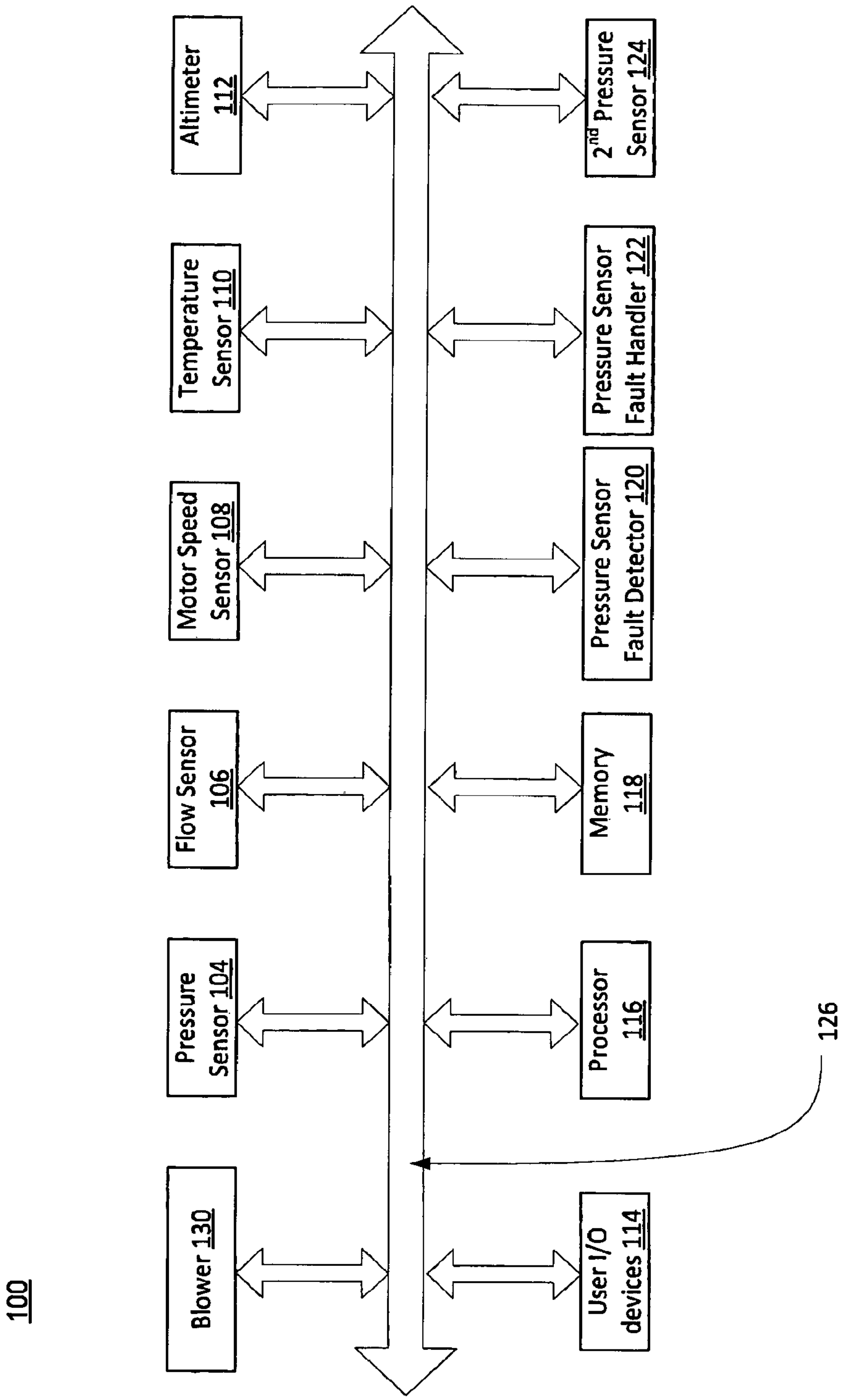
FIG. 2 is a block diagram of an example configuration of the respiratory apparatus of FIG. 1 with optional components.

FIG. 2 is a block diagram illustrating an example bus configuration of the respiratory apparatus 100 shown in FIG. 1. The apparatus 100 may include one or more of the following components: blower 130, a pressure sensor 104 (which may be located proximate to the mask or proximate to a blower or in both locations), a flow sensor 106, a motor speed sensor 108, a temperature sensor 110, an altimeter 112, user I/O devices 114, a processor 116, a memory 118, a pressure sensor fault detector 120, and a pressure sensor fault handler 122 and optionally a second pressure sensor 124. One or more of these components may be operatively connected with each other via wireless communication, physical coupling and/or electrical coupling, such as with a bus 126. One of more of these components may transmit or receive executable instructions in analog or digital signals to or from one or more of other components. Details with respect to each component are given below.

The flow generator 102 may be configured to generate breathable gas from a blower 130 (e.g., a motor and impeller) to a patient via a patient interface 132. The blower 130 may be a servo-controller blower such as a blower in a volute. An output of the flow generator 102 may be coupled to a patient interface 132, and a gas delivery conduit 134 that directs generated breathable gas between the blower 130 and the patient interface 132.

The flow generator 102 may be configured to generate breathable gas at different therapeutic pressure levels or flows. The flow generator 102, with a suitable controller, may adjust the blower 130 output by varying the current or voltage supplied to the motor. As discussed in more detail herein, the control of the operation of the blower 130 may be via a pressure control loop (i.e., control of measured pressure to satisfy a target/desired pressure set point), a flow control loop (i.e., control of measured flow to satisfy a target/desired flow set point) and/or a speed control loop (i.e., control of measured speed of the blower's motor to meet a target/desired speed set point).

Thus, the apparatus 100 may include a variety of sensors to observe or detect characteristics of the gas within the flow generator 102. The apparatus 100 may rely on readings provided by one or more of some sensors to determine accuracy of one or more of other sensors. Details of such monitoring with each sensor are given below.

For example, the apparatus 100 may include a pressure sensor 104 to detect pressure of the gas delivered by the flow generator 102. The pressure sensor 104 may be a pressure transducer that may produce a pressure signal proportional to a gas pressure associated with operation or use of the apparatus 100. The pressure sensor 104 may be positioned to measure the gas pressure at various positions with respect to the flow generator 102, such as, at the patient interface 132, at an outlet of the flow generator 102, or at the gas delivery conduit 134 or combinations thereof. For instance, as illustrated in FIG. 1, the pressure sensor 104 may be positioned at the patient interface 132, and in turn, may measure the gas pressure at the patient interface 132. Alternatively, the pressure sensor 104 may be positioned in the conduit 134, and in turn, may detect the gas pressure within the conduit 134. The pressure sensor 104 may also be positioned at the outlet of the flow generator 102, such that the pressure sensor 104 may measure the pressure of the gas immediately generated by the flow generator 102. Optionally, the pressure measurements may be adjusted to account for pressure drop within the system such as for estimating mask pressure when a pressure sensor measures pressure proximate to the outlet of the blower 130 of the flow generator 102. In such an arrangement a pressure drop along the air delivery tube may be predefined, estimated or calculated.

Optionally, the apparatus 100 may include a flow sensor 106 to detect flow, such as the flow attributable to the blower 130, any system or mask leak and/or patient respiratory flow.

The flow sensor 106 may include a pneumotachograph, a differential pressure transducer, or other similar devices to produce a flow signal or a flow reading representing the flow rate.

With continued reference to FIG. 1, the apparatus 100 may include a motor speed sensor 108 to detect the motor speed, e.g., the rotational speed, of the motor in the flow generator 102. The motor speed sensor 108 may include a Hall effect sensor or similar. A further example of a motor speed sensor 108 suitable for the present technology may be found in PCT/AU2005/001688 filed on Nov. 2, 2005, the entire disclosure of which is incorporated herein by reference. In some embodiments, by monitoring the motor speed and, optionally, the current supplied to the motor, a controller of the apparatus 100 may estimate the flow rate or the gas pressure.

In one embodiment, the apparatus 100 may optionally include a temperature sensor 110 to measure temperature of the gas delivered by the flow generator 102. The temperature sensor 110 may include a temperature transducer, such as a thermocouple or a resistance temperature detector (RTD). Depending on the placement of the temperature sensor 110, the temperature sensor 110 may measure the gas temperature at alternative positions within the flow generator 102. In one embodiment, as illustrated in FIG. 1, the temperature sensor 110 may be positioned at the blower 130 outlet, such as near the flow sensor 106, of the flow generator 102, and in turn, may measure the temperature of the gas immediately exiting the blower 130 of the flow generator 102. Alternatively the temperature sensor 110 may be positioned upstream of the blower, such as at the blower inlet or external to apparatus 100 to measure the temperature of the gas entering the blower or the ambient temperature. The temperature of the gas leaving the blower may then be estimated or calculated based on this measured inlet or ambient temperature.

With continued reference to FIG. 1, in some embodiments, the apparatus 100 may include an altimeter 112. The altimeter 112 may detect altitude of the apparatus 100, such as the altitude relative to a fixed level, e.g., sea level. The altimeter 12 may be positioned at any suitable location on or within the apparatus 100.

The apparatus 100 may optionally include user I/O devices 114 to facilitate user operation of the apparatus 100. A user of the apparatus 100 may be a physician, nurse, clinician, caretaker or patient. The user I/O devices 114 may include one or more of user input devices including, but not limited to, a keyboard, touch panel, control buttons, mouse, and switch. For example, such an I/O device may be implemented to accept input entered by a user such as an altitude of the apparatus 100.

The user I/O devices 114 may include a user output device, such as a display or alarms (not shown). The display may be a monitor or LCD panel. The display may display information regarding the status of the apparatus 100, e.g., the pressure of the gas delivered to the patient as obtained from the pressure sensor 104. Alternatively, the display may also display a status or warning message concerning accuracy or fault following testing of the operation of a sensor. The alarms may provide a warning alert via a sound and/or light e.g. LED light, to identify a fault condition.

In addition to the various sensors described above, the apparatus 100 may include a controller, such as a processor 116, to control operation of the processes related to the apparatus 100. The processor 116 may refer to a single processor or a collection of processors including one or more of the following: central processing unit (CPU), microprocessor, digital signal processor, front end processor, coprocessor, data processor, and/or analog signal processor. The processor 116 may be implemented with one or more application specific integrated circuits (ASICs). In one aspect, the apparatus 100 as a whole may have a processor 116 to perform acts of each component described herein in accordance with programmable instructions executed by the processor 116. Alternatively, one or more individual components of the apparatus 100, e.g., the pressure sensor fault detector 120 and the pressure sensor fault handler 122, may each have its own processor configured to execute component-specific instructions.

In some aspects, the processor 116 may be physically mounted within the apparatus 100. Alternatively, the processor 116 may be located remotely from the apparatus 100, and may communicate with the apparatus 100 via a network (not shown). When there are a collection of processors, one or more processors 116 may be physically mounted within the apparatus 100, while the remaining processors may communicate remotely with the apparatus 100 via a network.

In one embodiment, the apparatus 100 may include a memory 118 to store programmable instructions executable by the processor 116. The memory 118 may include a volatile memory, a non-volatile memory, or a combination thereof. The volatile memory may include a RAM, such as a dynamic random access memory (DRAM) or static random access memory (SRAM), or any other forms of alterable memory that may be electrically erased and reprogrammed. The non-volatile memory may include a ROM, a programmable logical array, or other forms of non-alterable memory which cannot be modified, or can be modified only slowly or with difficulty. The non-volatile memory may include firmware.

Further, embodiments of the present technology may include one or more detectors to assess accuracy of one or more sensors described above, or determine if a fault has occurred in one or more sensors. For instance, the apparatus 100 may include a pressure sensor fault detector 120 that implements algorithms to assess accuracy of the pressure sensor 104. The algorithms may be implemented in programmable instructions executable by the processor 116. The programmable instructions may be stored in the memory 118, such as firmware, or a data storage (not shown) of the apparatus 100 or may otherwise be implemented as one or more ASICs.

Sensor Evaluation

To evaluate accuracy of the pressure sensor 104, the detector 120 may receive measurements from one or more of the sensors 104-112 described above. One or more of the sensors 104-112 may provide measurements to the detector 120 in real time or quasi-real time, or on demand.

Figure 3:
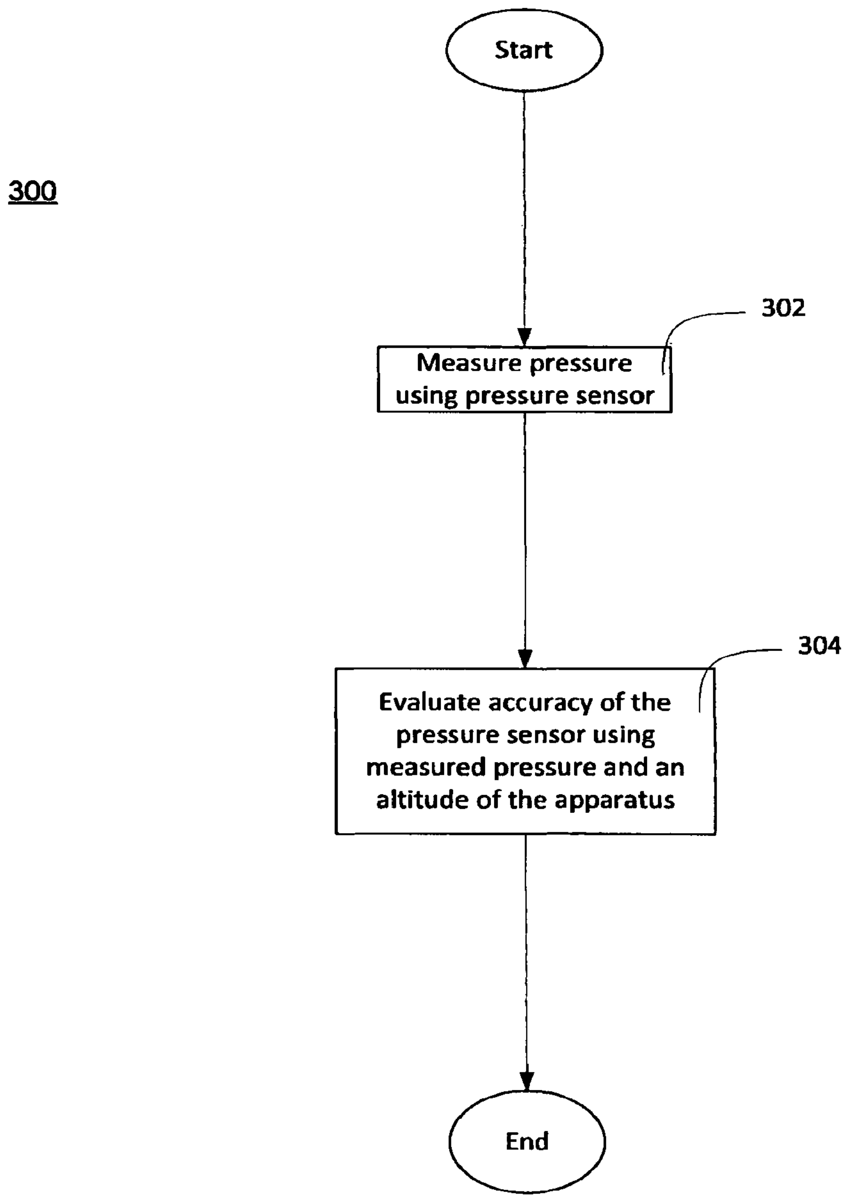
FIG. 3 is a flow diagram illustrating an example methodology for a controller to determine accuracy of operation of a pressure sensor.

FIG. 3 is a flowchart 300 illustrating a suitable process performed by the detector 120 to evaluate accuracy of the pressure sensor 104. Although steps discussed herein are made in reference to the detector 120, one or more of these steps may be performed by the processor 116.

At 302, the detector 120 may obtain a pressure measure from the pressure sensor 104. At 304, the detector 120 may evaluate accuracy of the pressure sensor 104 based on the pressure measure and an altitude of the apparatus 100. The altitude of the apparatus 100 may include one or more of (1) a previously calculated altitude estimate from a prior pressure measure of the apparatus 100, (2) an expected altitude or altitude range for the apparatus 100, (3) an actual or expected altitude input into the apparatus 100 for operation;

and/or (4) an altitude measured by an altimeter 112 of the apparatus 100. The detector 120 may calculate an altitude estimate based on the pressure measure, and compare the altitude estimate to any one or more of the altitudes (1)-(4) described above.

Optionally, the detector 120 may evaluate the accuracy of the pressure sensor 104 by comparing the pressure measure and a calculated estimate of pressure that is based on a previously calculated altitude estimate.

Based on the comparison, the detector 120 may determine whether the operation of the sensor 104 is accurate or faulty. For example, if the compared values are identical or substantially similar to each other, the sensor 104 may be deemed accurate. By contrast, if the compared values are different or substantially different, the sensor may be deemed faulty.

Various example embodiments of the detector 120 and its processes are discussed in more detail herein with reference to FIGS. 4-12.

Figure 4:
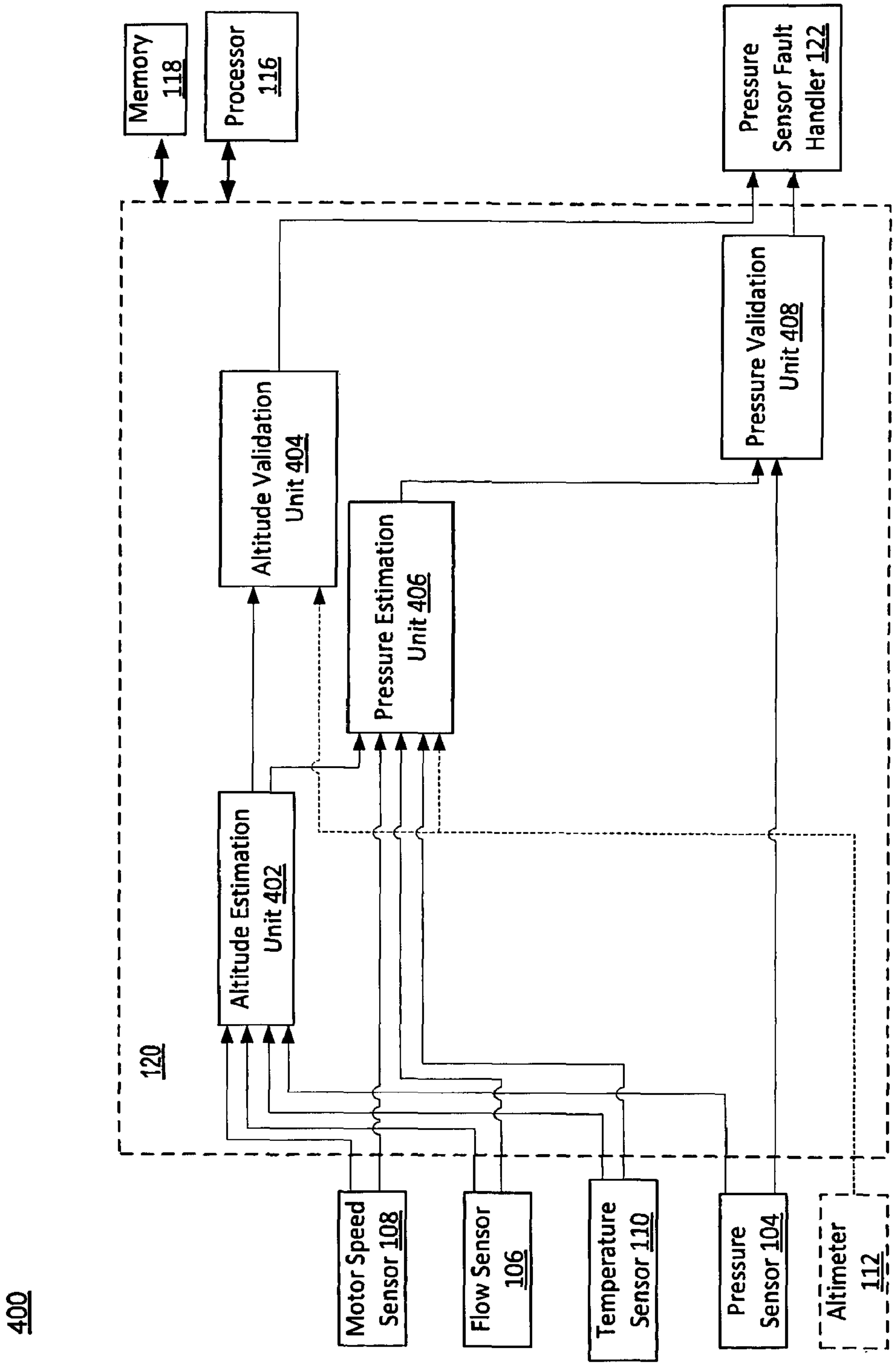
FIG. 4 is a block diagram of an example configuration of a pressure sensor fault detector.

FIG. 4 is a block diagram 400 illustrating an example configuration of the detector 120. In some embodiments, the detector 120 may include one or more of the following components: an altitude estimation unit 402, an altitude validation unit 404, a pressure estimation unit 406 and a pressure validation unit 408. One or more of these units 402-408 may obtain measurements from one or more of the sensors 104-112: namely pressure sensor 104, temperature sensor 110; motor speed sensor 108; flow sensor 106; and altimeter 112. One or more of these units 402-408 may evaluate an accuracy of the pressure sensor 104 based on the measurements obtained from one or more of the sensors 104-112. Example operations with respect to each unit are as follows.

The altitude estimation unit 402 may estimate altitude of the apparatus 100 based on measurements obtained from one or more of the sensors 104-110: pressure sensor 104, temperature sensor 110; motor speed sensor 108; and flow sensor 106.

In one embodiment, the altitude estimation unit 402 may calculate an estimate of the altitude during operation of the apparatus 100 as a function of some or all of the following: the measured pressure of the gas obtained from the pressure sensor 104, the measured flow rate of the gas obtained the flow sensor 106, the measured temperature obtained from the temperature sensor 110, and the measured motor speed obtained from the motor speed sensor 108. For example, the altitude estimation unit 402 may compute the altitude of the apparatus 100 according to the following function:

$$h=f_x(P,T \text{ and } \omega)$$

where:

h is the estimated altitude;

P is the measure of pressure;

T is an optional measure of temperature that in some embodiments may be omitted; and ω is a measure of motor speed.

$f_x$ is a polynomial function (e.g., $y=Ax^2+Bx+c$ of a suitable degree depending on the constants and parameters of the function) applied to the measured values that may be derived empirically, such as by a Gray Box Model or best fit model using suitable test data. In a case where a measure of flow is not implemented in the function as listed in the example above, the measurements applied to the function may be obtained during operation of the apparatus 100 while a controller, e.g., the processor 116, of the apparatus 100 controls the motor of the blower 130 to deliver a constant flow rate such as by controlling the blower 130 by a flow control loop and setting a fixed flow set point. An example flow set point may be in a range from 10 to 60 liters/minute, such as a flow rate set point of 20 liters/minute. Such a fixed operation may optionally be performed by the apparatus 100 as a start-up or pre-treatment procedure and may take place while the apparatus 100 is not being used by a patient/user (i.e., without the patient interface 132 on the patient). Such a fixed operation may serve to simplify the parameters of the function for calculating the altitude. Alternatively, in some embodiments, the measurement operation may be conducted while the detector 120 controls a constant motor speed rather than controlling a constant flow rate. In such a case, the measured flow may be utilized in the above function rather than the measured motor speed, though both may be utilized.

From Fan Law for a centrifugal blower, pressure P at the outlet at zero flow is given by:

$$P=\frac{\rho\omega^2}{2}\left(r_{bladeend}^2-r_{bladestart}^2\right)$$

ω is motor speed (e.g., rotational speed);

ρ is air density;

$r_{bladeend}$ is the radius of the circle traced by the end of the impeller blade; and $r_{bladestart}$ is the radius of the circle traced by the start of the impeller blade.

Assume an empirical form for pressure derived from the Fan Law above at constant flow as:

$$P \cong \varphi\rho\omega^2+(\delta+\theta h)\omega$$

Where φ, δ and θ are constants.

Typically centrifugal blowers have dropping fan curves (as seen in literature) hence pressure at any flow (Q) can be approximated as:

$$P \cong \alpha\cdot(\varphi_2\cdot Q^2+\varphi_1\cdot Q+\varphi_0)\rho\cdot\omega^2+[(\delta_2\cdot Q^2+\delta_1\cdot Q+\delta_0)+(\theta_2\cdot Q^2+\theta_1\cdot Q+\theta_0)\cdot h]\omega \quad \text{(A1)}$$

Where $\varphi_2$, $\varphi_1$, $\varphi_0$, $\theta_2$, $\theta_1$, $\theta_0$, $\delta_2$, $\delta_1$ and $\delta_0$ can be determined empirically from test data including various combinations of altitudes, motor speed, flow rates, and pressure.

By neglecting the effects of humidity and local air temperature, air density can be written as a function of altitude using the values for the International Standard Atmosphere and the universal gas constant.

The absolute temperature (T) at altitude (h) meters above sea level may be given by:

$$T=T_0-L\cdot h; \text{ and}$$

The pressure (p) at altitude (h) is given by:

$$p=p_0\cdot\left(1-\frac{L\cdot h}{T_0}\right)^{\frac{g\cdot M}{R\cdot L}};$$

where:

$T_0$ is the sea level standard temperature (e.g. 288.15K);

L is the temperature lapse rate (e.g. 0.0065K/m);

R is the universal gas constant (e.g. 8.31447 J/(mol*K);

M is the molar mass of dry air (e.g. 0.0289644 Kg/mol);

$p_0$ is a sea level standard atmospheric pressure (e.g. 101325 Pa); and g is the earth surface gravitational acceleration (e.g. 9.80665 m/s$^2$).

The air density (ρ)(Kg/m$^3$) can be calculated by the following:

$$\rho = \frac{p \cdot M}{R \cdot T}$$

In some cases, this density equation may be simplified by approximating density as a linear function of altitude. Such a simplification may be performed to maintain the pressure model (A1) linear with altitude and to allow calculation of altitude without the need for expensive computations. The simplified air density approximation was determined to have a low error rate, i.e. to be sufficiently accurate, within the range of altitudes at which a respiratory apparatus is commonly used, such as below 9,000 feet above sea level. A simplified air density approximation is as follows:

$$\rho \cong \alpha \cdot (1 - 4 \cdot \beta \cdot h) \qquad \text{(D1)}$$

where:

$$\alpha = \frac{P_0 \cdot M}{R \cdot T_0}; \text{ and} \qquad \text{(D2)}$$

$$\beta = \frac{L}{T_0} \qquad \text{(D3)}$$

ρ is the air density (Kg/$m^3$);

$P_0$ is a sea level standard atmospheric pressure (e.g., 101325 Pa);

M is the molar mass of dry air (e.g., 0.0289644 Kg/mol);

R is the universal gas constant (e.g., 8.31447 K/(mol*K);

$T_0$ is the sea level standard temperature (e.g., 288.15K); and

L is the temperature lapse rate (e.g. 0.0065K/m).

Making use of the above simplification for air density (A1) can re-written as:

$$P \cong \alpha \cdot (\varphi_2 \cdot Q^2 + \varphi_1 \cdot Q + \varphi_0)(1 - 4 \cdot \beta \cdot h) \cdot \omega^2 + [(\delta_2 \cdot Q^2 + \delta_1 \cdot Q + \delta_0) + (\theta_2 \cdot Q^2 + \theta_1 \cdot Q + \theta_0) \cdot h]\omega \qquad \text{(A2)}$$

Function $f_x$ to compute the altitude of the apparatus 100 may be implemented without a temperature measure, such as if no temperature sensor is implemented by the apparatus 100, by solving for h in (A2):

$$h \cong \frac{P - [\alpha(\varphi_2 \cdot Q^2 + \varphi_1 \cdot Q + \varphi_0)\omega^2 + (\delta_2 \cdot Q^2 + \delta_1 \cdot Q + \delta_0) \cdot \omega]}{(\theta_2 \cdot Q^2 + \theta_1 \cdot Q + \theta_0) \cdot \omega - 4\alpha\beta(\varphi_2 \cdot Q^2 + \varphi_1 \cdot Q + \varphi_0)\omega^2} \qquad \text{(A3)}$$

where:

h is the estimated altitude;

P is the measured pressure;

Q is the measured flow; and

ω is the measured motor speed (e.g., rotational speed).

$\varphi_2$, $\varphi_1$, $\varphi_0$, $\theta_2$, $\theta_1$, $\theta_0$, $\delta_2$, $\delta_1$ and $\delta_0$ may be constants that are predetermined empirically with a set of test data including various combinations of altitudes, motor speed, flow rates, and pressure.

In some embodiments, the function $f_x$ to compute the altitude of the apparatus 100 may take into account the temperature. Specifically, the motor speed $\omega_{temp}$ under the influence of the temperature may substitute for co in equation A1, where $\omega_{temp}$ may be a function of the measured temperature and the measured motor speed as follows:

$$\omega_{temp} = \omega + \chi_n \cdot T^n + \chi_{n-1} \cdot T^{n-4} + \chi_1 \cdot T + \chi_0 \qquad \text{(A4)}$$

where:

ω is the measured motor speed; and

Tis the measured temperature.

Here, $\chi_n$, $\chi_{n-1}$, . . . , $\chi_1$, $\chi_0$, along with other constants $\varphi_2$, $\varphi_1$, $\varphi_0$, $\theta_2$, $\theta_1$, $\theta_0$, $\delta_2$, $\delta_1$ and $\delta_0$ can be determined empirically from test data including various combinations of altitudes, motor speed, flow rates, and pressure.

In some embodiments, to increase accuracy or reliability of estimation, the altitude estimation unit 402 may estimate the altitude of the apparatus 100 for a predetermined number of times, e.g., 2, 3, 4, 5, 6, 7, 8, 9, 10 times or more, and calculate an average of the estimates. For instance, the altitude estimation unit 402 may take measurements from the pressure sensor 104, flow sensor 106, motor speed sensor 108, and optionally, temperature sensor 110 at a predetermined frequency over a predetermined period of time. The altitude estimation unit 402 may calculate an estimated altitude based on the measurements at the same frequency, and calculate an average of the estimated altitudes over the predetermined period of time. The averaging process may improve reliability of the estimation by reducing the effect of variability of input sensor signals, and by reducing artifacts within the signals. The altitude estimation unit 402 may provide the average estimation to the altitude validation unit 404, which, in turn, may determine validity or plausibility of the average estimated altitude.

After calculating the altitude of the apparatus 100, the altitude estimation unit 402 may output the estimated altitude to the altitude validation unit 404. The altitude validation unit 404 may then evaluate accuracy or plausibility of the estimated altitude. For example, the altitude validation unit 404 may evaluate the accuracy or plausibility of the estimated altitude (and thereby evaluate the sensor) by comparing the estimate to a threshold. An implausible or inaccurate estimated altitude, or an average estimated altitude, may be taken as a suggestion that at least one measurement obtained from one sensor used in computing the altitude is erroneous. If the flow sensor 106, the motor speed sensor 108, and optionally, the temperature sensor 110 are presumed accurate, an inaccurate or implausible estimated altitude may suggest that the pressure measurement obtained from the pressure sensor 104 is incorrect, or the pressure sensor 104 is inaccurate. A slight error in the pressure sensor 104 may significantly affect the quantity of the estimated altitude.

In one example, the threshold test may involve a range of altitudes in which the apparatus 100 may operate, including a maximum altitude and a minimum altitude. In such a case, the apparatus 100 may be implemented without an altimeter. Such altitudes may, for example, be in a range from 0 to 9000 feet above sea level or from 500 feet below sea level to 10,000 feet above sea level. Other ranges may be used for such a range-based threshold test. When the estimated altitude falls outside the range of altitudes, the estimated altitude may be deemed implausible, which, in turn, may suggest that the pressure sensor 104 is inaccurate. Otherwise, if the estimated altitude is within the range, the pressure sensor 104 may be taken as being sufficiently accurate or operable for controlling pressure with the apparatus 100.

In another example, the threshold may be an altitude reading obtained from the altimeter 112, in the event that apparatus 100 is provided with an altimeter. The altitude validation unit 404 may evaluate plausibility of the estimated altitude by comparing it to the altitude reading of the altimeter 112. When the estimated altitude differs significantly from the altitude reading by an offset greater than a predetermined difference, e.g., 500 feet, 600 feet, 700 feet, 800 feet or 900 feet, the estimated altitude may be deemed inaccurate, which, in turn, may suggest that the pressure sensor 104 is inaccurate. If the estimated altitude does not differ significantly from the altitude reading, the pressure sensor 104 may be taken as being sufficiently accurate or operable for controlling pressure with the apparatus 100.

In a further example, the threshold may be an altitude previously calculated by the altitude estimation unit 402, such as in the case that no altimeter is implemented. The previously calculated altitude estimate may have been previously validated by the altitude validation unit 404. The previously calculated altitude estimate may be designated as the current altitude of the apparatus 100. In this regard, the previously calculated altitude estimate may have been stored in the memory 118 as result of a previous validation. In this example, the altitude validation unit 404 may receive the estimated altitude output by the altitude estimation unit 402, and compare it to the current altitude of the apparatus 100, e.g., the previously calculated altitude estimate. When the estimated altitude is not the same, or if it differs from the previously calculated altitude estimate by an offset greater than a predetermined difference, e.g., 400 feet, 500 feet, 600 feet, 700 feet, 800 feet or 900 feet, the estimated altitude may be deemed inaccurate, which, in turn, may be taken as a suggestion that the pressure sensor 104 is no longer accurate. Otherwise, if the estimated altitude is the same as the previously calculated altitude estimate or if it does not differ significantly from the previously calculated altitude estimate, the pressure sensor 104 may be taken as still being sufficiently accurate or operable for controlling pressure with the apparatus 100.

If the estimated altitude is deemed implausible or inaccurate, the altitude validation unit 404 may output a signal indicating that the pressure sensor 104 is inaccurate, or a fault has occurred in the pressure sensor 104. The altitude validation unit 404 may output the signal to the pressure sensor fault handler 122 for further execution.

When the estimated altitude is deemed plausible or accurate, the altitude validation unit 404 may output a signal indicating that the pressure sensor 104 is accurate, or no fault has occurred in the pressure sensor 104.

With continued reference to FIG. 4, the detector 120 may optionally include a pressure estimation unit 406 and a pressure validation unit 408. The pressure estimation unit 406 may calculate an expected estimate of a pressure. The pressure estimation unit 406 may estimate the expected pressure from measurements obtained from one or more of the various sensors; temperature sensor 110, motor speed sensor 108, and flow sensor 106.

For example, the pressure estimation unit 406 may estimate the expected pressure from some or all of the following: the measured flow rate of the gas obtained from the flow sensor 106, the measured motor speed obtained from the motor speed sensor 108, and the altitude of the apparatus 100, such as a previously calculated altitude or a measured altitude from an altimeter 112. The pressure estimation unit 406 may calculate the expected pressure according to a function:

$$P_e = f_x(h\ Q, T \text{ and } \omega)$$

where:

$P_e$ is the estimate of expected pressure;

h is an estimate, measure or input altitude;

Q is a measure of flow;

T is an optional measure of temperature that in some embodiments may be omitted; and ω is a measure of motor speed.

$f_x$ is a polynomial function (e.g., $y=Ax^2+Bx+c$ of a suitable degree depending on the constants and parameters of the function) applied to the measured values that may be derived empirically, such as by a Gray Box Model or best fit model using suitable test data. Such measurements for the determination of pressure with such a function may be made periodically (e.g., on a measurement cycle of 1, 2, 3, 4, 5, 6, 7, 8, 9 or 10 hertz rate) during operation of the apparatus 100, such as during use or treatment, and may optionally be performed by the apparatus 100 as a start-up or pre-treatment procedure and may take place while the apparatus 100 is not being used by a patient/user (i.e., without the patient interface 132 on the patient) or both during patient use and patient non-use operation.

In one example, the function may be implemented without a temperature measure, such as if no temperature sensor is implemented, as follows (from (A2)):

$$P \cong \alpha\cdot(\varphi_2\cdot Q^2+\varphi_1\cdot Q+\varphi_0)(1-4\cdot\beta\cdot h)\cdot\omega^2+[(\delta_2\cdot Q^2+\delta_1\cdot Q+\delta_0)+(\theta_2\cdot Q^2+\theta_1\cdot Q+\theta_0)\cdot h]\omega \quad \text{(B1)}$$

where:

$P_e$ is the expected pressure;

Q is the measured flow;

ω is the measured motor speed;

h is an altitude;

α is defined according to equation D2 above; and

β is defined according to equation D3 above.

In the above function, $\varphi_2$, $\varphi_1$, $\varphi_0$, $\theta_2$, $\theta_1$, $\theta_0$, $\delta_2$, $\delta_1$ and $\delta_0$ may be constants that are predetermined empirically from a set of test data including various combinations of altitudes, motor speed, flow rates, and pressure.

In one example, h may be a value obtained from the altimeter 112 if implemented. In another example, h may be the altitude of the apparatus 100 previously calculated by the altitude estimation unit 402 and stored in the memory 118. The previously calculated altitude may be validated by the altitude validation unit 404 and designated as the current altitude of the apparatus 100.

In another example of the function, such as in the case that a measure of temperature is available, the pressure estimation unit 406 may take into consideration the measured temperature of the gas obtained from the temperature sensor 110. The expected pressure may then be calculated according to a function such as the equation B1 with $\omega_{temp}$ being substituted for ω in equation B1. The function $\omega_{temp}$ is a function of measured temperature T and measured motor speed ω as described above in equation A3.

In some embodiments, the pressure estimation unit 406 may be configured to start estimation of the pressure or the timing of the measurement of values for the function based on one or more of the following: flow rate, flow derivative, motor speed and instantaneous acceleration of the motor speed (i.e. rotor acceleration). For example, the measurements for the application of the pressure estimation unit 406 may be taken at a certain motor speed, a certain flow rate, a certain flow derivative (e.g., approximately zero such as during detection of an end expiratory pause) or certain acceleration of the motor speed (e.g., approximately zero).

In one such example, the pressure estimation unit 402 may perform estimation of the pressure when the apparatus 100 reaches a steady state condition, e.g., when the flow generator 102 operates generally constantly at a predetermined speed. For instance, the pressure estimation unit 402 may determine the instantaneous acceleration of the flow generator 102. If the instantaneous acceleration is small or negligible, the motor speed may be deemed steady.

After calculating the expected pressure, the pressure estimation unit 406 may output the expected pressure to the pressure validation unit 408. The pressure validation unit 408 may validate an actual reading obtained from the pressure sensor 104, i.e., the measured pressure, against the expected pressure.

When the actual reading obtained from the pressure sensor 104 deviates from the expected pressure such as if they are not equal or if their difference exceeds a predetermined threshold, e.g., 5 $cmH_2O$, the pressure sensor 104 may be deemed inaccurate (e.g., if $(|P_{meas}-P_{est}|)>5$ $cmH_2O$). The pressure validation unit 408 may output a signal indicating that the pressure sensor 104 is inaccurate to the pressure sensor fault handler 122 for further execution.

However, if the difference between the measured pressure and the expected pressure is equal to or less than the predetermined threshold, the pressure sensor 104 may be deemed accurate (e.g., if $((|P_{meas}-P_{est}|)$ 5 $cmH_2O$). The pressure validation unit 408 may output a signal indicating that the pressure sensor 104 is accurate, or no fault has occurred in the pressure sensor 104.

It is to be understood that the predetermined threshold may include other limits such as 1 cm $H_2O$, 2 $cmH_2O$, 3 $cmH_2O$, 4 $cmH_2O$, or 6 $cmH_2O$ or similar such limits. In some cases, the predetermined threshold may include limits determined from relative values rather than absolute values. For instance, the threshold may be a function of the expected or measured pressure. For example, the predetermined threshold may be determined using a portion or percentage of the expected pressure. Other thresholds described in this specification may be similarly derived as functions of other values.

In an example embodiment, the detector 120 may execute an initial test of the pressure sensor 104 prior to therapeutic treatment to the patient, such as part of an initialization procedure. Thereafter, the detector 120 may execute one or more periodic tests of the pressure sensor 104 after therapeutic treatment commences. Detailed implementations of various test procedures performed by detector 120 are discussed below with reference to FIGS. 5-12. Unless otherwise indicated, any of the procedures described below may be performed before or during therapeutic treatment to the patient. Further, unless otherwise indicated, the procedures described below may be performed in an initial test, one or more of periodic tests, or the combination thereof.

Figure 5:
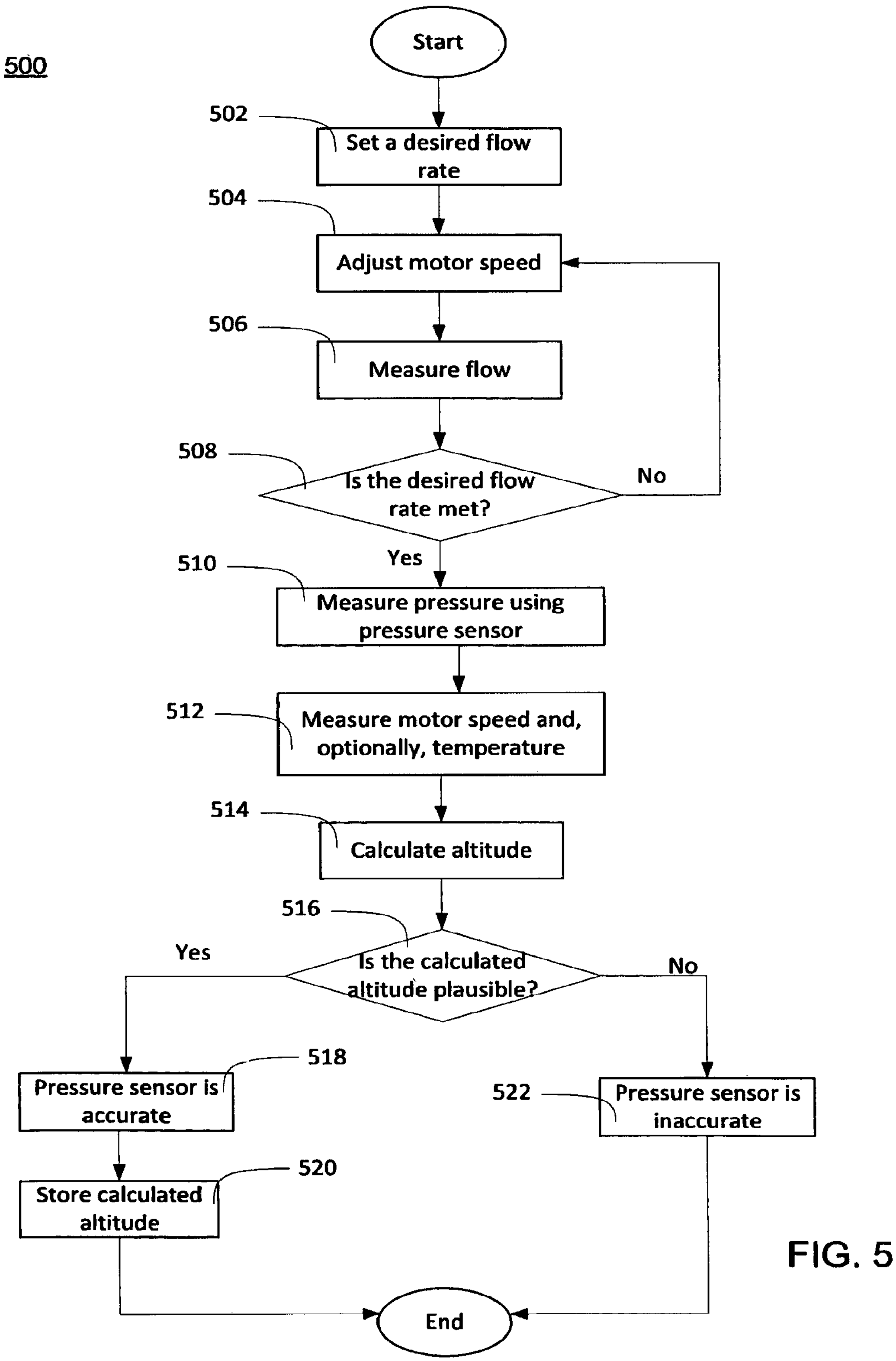
FIG. 5 is a flow diagram illustrating another methodology for a controller to determine accuracy of a pressure sensor.

FIG. 5 is a flowchart 500 illustrating a test procedure that may be performed by the detector 120 as an initialization procedure for the apparatus 100. At 502, the detector 120 may set a predetermined flow rate for delivery by a blower 130 of the flow generator 102. For example, the predetermined flow rate may be a flow rate of 20 liters/minute, or a low flow rate that is below 50 liters/minute. Alternatively, the predetermined flow rate may be in a range between about 10 liters/minute and about 60 liters/minute. In one embodiment, the predetermined flow rate may be manually entered by a user at initialization of the apparatus 100, e.g., when the apparatus 100 is powered on. In another embodiment, the predetermined flow rate may be a pre-set parameter for the methodology of the initialization procedure such as a value recorded in the memory 118.

Thereafter, between 504 and 508, the detector 120 may control the flow generator 102 to adjust the motor speed until the measured flow rate obtained from the flow sensor 106 meets the predetermined flow rate. In one embodiment, after the apparatus 100 powers on, the flow generator 102 may gradually increase the motor speed. Specifically, at step 504, the flow generator 102 may increase the motor speed in a predetermined increment at a predetermined frequency. After each increment, at step 506, the detector 120 may take a reading from the flow sensor 106 which represents the measured flow rate. At step 508, the detector 120 may compare the measured flow rate to the predetermined flow rate. If the measured flow rate is below the predetermined flow rate, the detector 120 may proceed back to step 504, at which point, the flow generator 102 may continuously increase the motor speed.

Once the measured flow rate reaches the predetermined flow rate, the altitude estimation unit 402 of the detector 120 may proceed to the next step 510.

Steps 502-508 are one example for controlling the blower 130 by using a flow control loop so as to operate the blower 130 at a constant or fixed flow rate. Alternatively, as previously mentioned, the blower 130 may be controlled via a motor speed control loop so as to operate the blower 130 to maintain a constant/fixed motor speed rather than a constant or fixed flow rate.

At 510-512, the detector 120 may make measurements from various sensors including: the pressure sensor 104, the motor speed sensor 108, and, optionally, the temperature sensor 110. Thereafter, at 514, the altitude estimation unit 402 may determine or calculate the altitude of the apparatus 100 from the measurements using a suitable function such as one based on function A1 or a look-up table with data derived from such a function.

Subsequently, at 516, the altitude validation unit 404 may evaluate the plausibility of the altitude calculated at 514. In one example, the altitude validation unit 404 may evaluate the calculated altitude by comparing the altitude calculated at 514 to a predetermined range of expected altitudes, examples of which are discussed earlier. In such a case, the apparatus 100 may be implemented without an altimeter. If the calculated altitude falls outside the predetermined range, the calculated altitude may be deemed implausible or inaccurate. Otherwise, if the calculated altitude falls within the predetermined range of expected altitudes, the calculated altitude may be deemed plausible and the pressure sensor may be deemed acceptable for normal operation of the apparatus 100.

Alternatively, the altitude validation unit 404 may evaluate the plausibility of the calculated altitude by comparing the calculated altitude to a reading of the altimeter 112 if implemented in the apparatus 100. The reading of the altimeter 112 may represent an accurate measurement of the altitude of the apparatus 100. If the altitude calculated at 514 differs from the measured altitude by more than a predetermined amount, e.g., 600 feet or 900 feet, then the calculated altitude may be taken as inaccurate and the pressure sensor may be deemed not suitable for normal operation. Otherwise, the calculated altitude may be taken as acceptable and the pressure sensor may then be deemed suitable for normal operation.

In another embodiment, the altitude validation unit 404 may evaluate the plausibility of the altitude calculated at 514 by comparing it to a previously determined altitude, such as one determined from a previous session with the apparatus 100. The previously determined altitude may be retrieved from the memory 118. The previously determined altitude may be calculated by the altitude estimation unit 402 in a previous test procedure. The previously determined altitude may have been validated by the altitude validation 404 in the previous test. The previously determined altitude may be taken to represent the current altitude of the apparatus 100. If the altitude calculated at 514 differs from the previously determined altitude by a predetermined amount or threshold, e.g., 400 feet, 500 feet, 600 feet, 700 feet, 800 feet or 900 feet, then the presently calculated altitude may be taken as inaccurate, and the pressure sensor may be deemed unsuitable for normal operation of the apparatus 100. Otherwise, the calculated altitude may be taken as acceptable, and the pressure sensor 104 may be deemed suitable for operation.

Once the calculated altitude is deemed implausible or unacceptable, then at 522, the altitude validation unit 404 may output a signal indicating that the pressure sensor 104 is inaccurate or not suitable for normal operation. By contrast, if the calculated altitude is deemed plausible or acceptable, then at 518, the altitude validation unit 404 may output a signal indicating that the pressure sensor 104 is accurate or suitable for normal operation. When the calculated altitude is deemed plausible, the detector 120 may optionally, at step 520, store the calculated altitude in the memory 118. The calculated altitude may be subsequently retrieved from the memory 118 during one or more periodic test procedures.

In the example flow chart of the test procedure illustrated in FIG. 5, the process of the apparatus 100 may evaluate the pressure sensor 104 using one cycle of analysis, which may include one instance of each of the following: taking a pressure measurement using the pressure sensor 104, taking a motor speed measurement using the motor speed sensor 108, optionally taking a temperature measurement using the temperature sensor 110, and calculating or determining the altitude based on these measurements and evaluating the calculated altitude.

Figure 6:
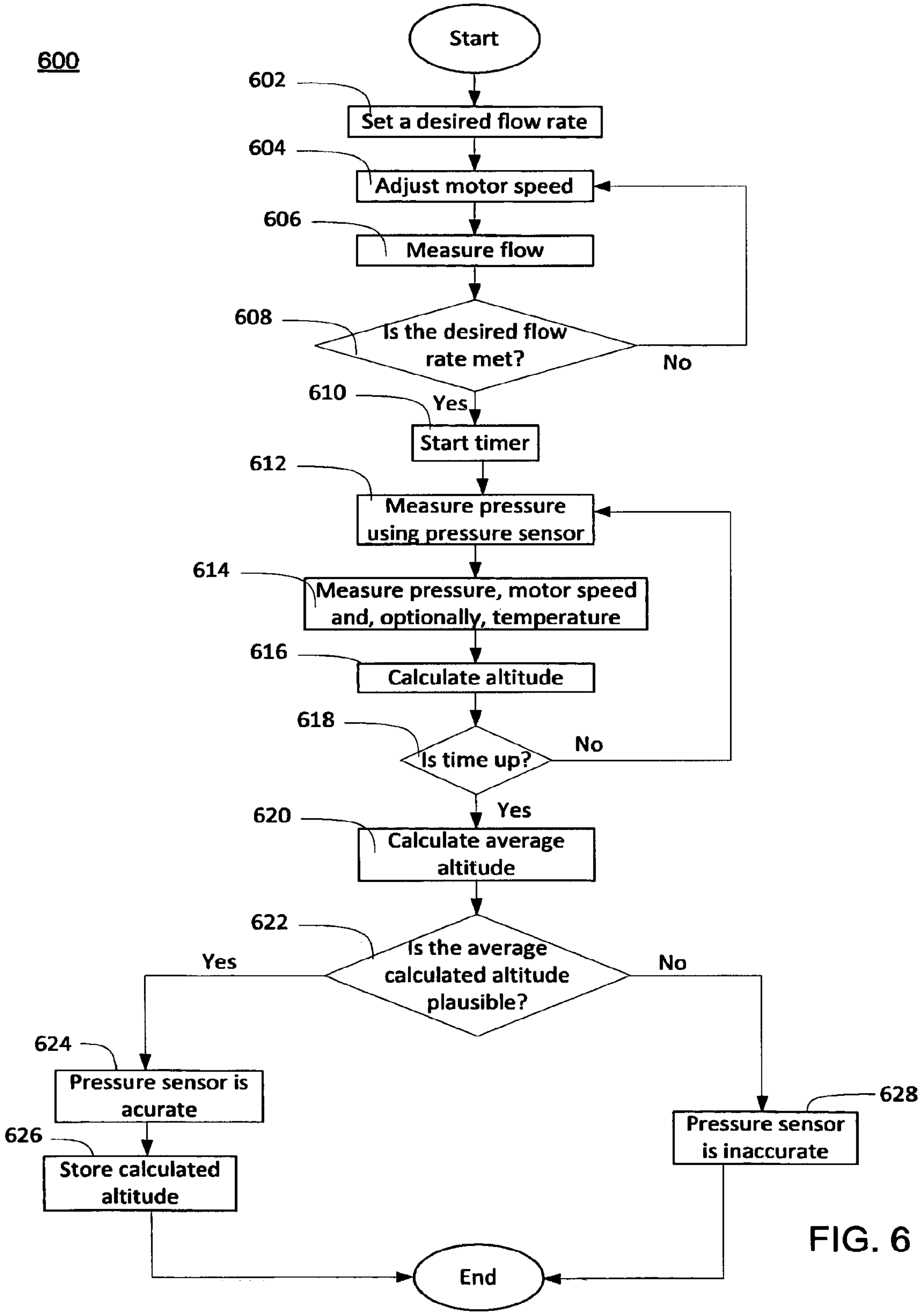
FIG. 6 is a flow diagram illustrating a method for determining accuracy of the pressure sensor according to another embodiment.

FIG. 6 illustrates an alternate flow chart 600 embodiment to the test procedure illustrated in FIG. 5. In this embodiment, the detector 120 may take a fault-tolerant approach to assess accuracy of the pressure sensor 104 such as by utilizing averages. For instance, the detector 120 may determine accuracy of the pressure sensor 104 based on a collective result of multiple cycles of analysis. Each cycle of analysis may be identical to that described above with respect to FIG. 5. Each cycle of analysis may occur at a predetermined frequency. For example, the predetermined frequency may be between 1 and 10 hertz, such as 1, 2, 3, 4, 5, 6, 7, 8, 9 or 10 hertz sampling rate. The collective result may be an average calculated altitude obtained from multiple cycles of analysis that occur within a predetermined period of time. The predetermined period of time may be, for example, 5, 10, 15, 20 or 30 seconds or longer or shorter periods of time. In the illustrated example, the detector 120 may include a timer to trigger multiple cycles for analysis or otherwise may implement a repeated measurement loop. The pressure sensor 104 may be determined suitable for normal operation or not when an average of calculated altitudes, or a calculated altitude from averaged measurements, determined from multiple cycles is evaluated as previously described.

As shown in FIG. 6, the processes of 602-608 may be identical to 502-508 of FIG. 5. At 610, the detector 120 may start a timer for the multiple cycles of analysis. Subsequently, the altitude estimation unit 402 may perform at 612-616 in the manner described with reference to 510-514 of FIG. 5. An iteration of 612-616 may be considered one cycle of analysis. The detector 120 may repeatedly iterate 612-616 to perform multiple cycles of analysis, until a predetermined amount of time, e.g., 5 seconds, has elapsed since the start of the timer as determined at 618.

Thereafter, at 620, the altitude estimation unit 402 may calculate an average of the altitudes calculated during the multiple cycles of analysis. The altitude estimation unit 402 may output the average to the altitude validation unit 404.

Then, at 622-628, the altitude validation unit 404 may determine suitability of the pressure sensor 104 based on plausibility of the average altitude as previously described with reference to 516-522 of FIG. 5.

In another embodiment, the timer 610 may be replaced with a counter configured to count the number of cycles and step 618 may determine if the desired number of cycles have been performed. In such an arrangement the detector 120 may assess accuracy of the pressure sensor 104 based on a predetermined number of cycles of analysis, e.g., at least 2 cycles of analysis or 5-10 cycles of analysis or more. The predetermined number of cycles may or may not be consecutive. For example, the detector 120 may conclude that the pressure sensor 104 is not suitable for normal operation when the altitude calculated is deemed implausible in each of 5-10 consecutive cycles of analysis. Alternatively, the detector 120 may conclude that the pressure sensor 104 is inaccurate when an average of the altitudes calculated in the 5-10 cycles of analysis is determined implausible.

Figure 7:
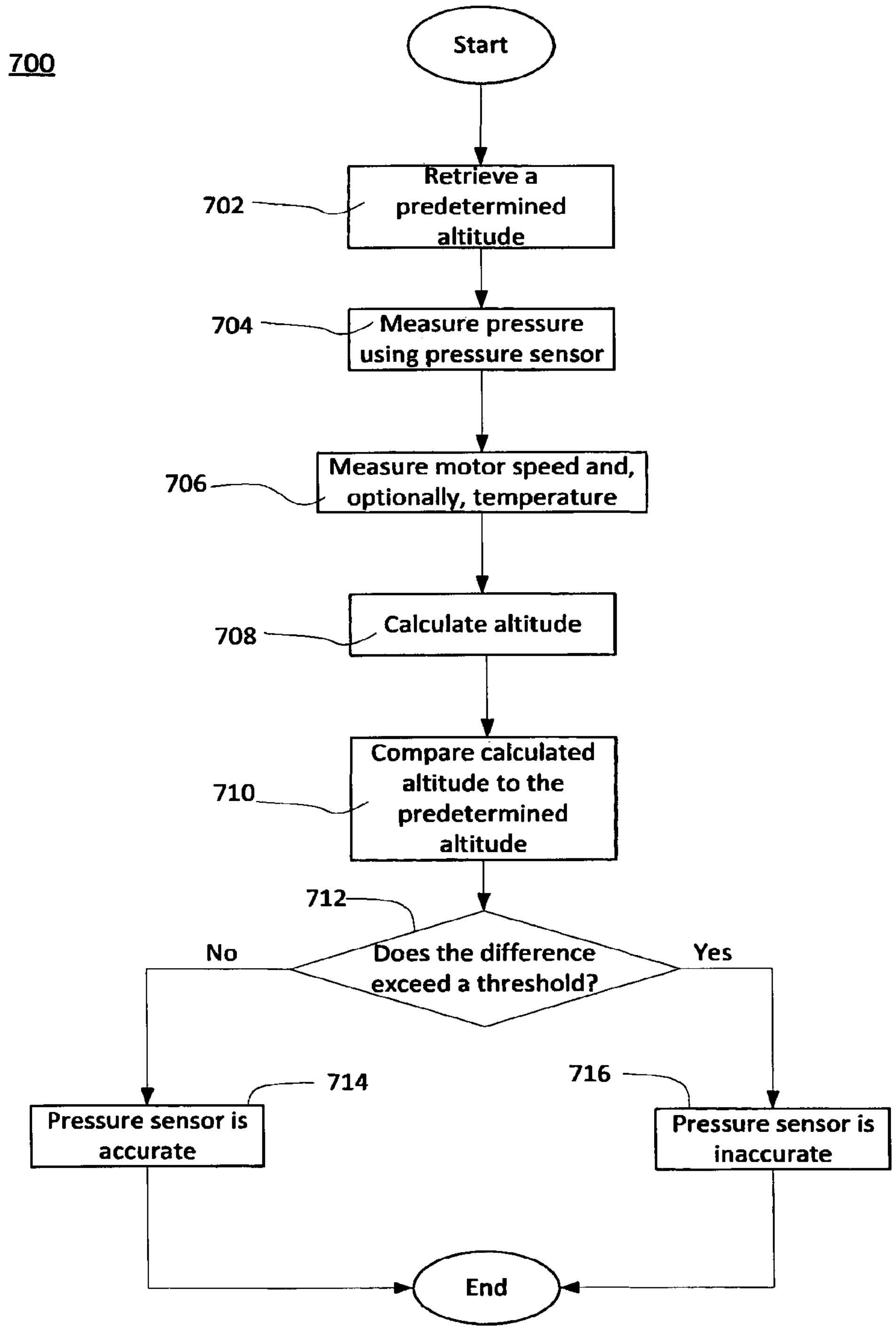
FIG. 7 is a flow diagram illustrating a method for determining accuracy of the pressure sensor according to yet another embodiment.

Subsequent to an initialization procedure, the detector 120 may periodically (e.g., continuously) monitor the accuracy of the pressure sensor 104 in one or more test procedures as the apparatus 100 provides therapeutic treatment to the patient. FIG. 7 illustrates a flowchart 700 of a periodic test procedure according to one such embodiment. At 702, the detector 120 or the altitude validation unit 404 may retrieve a predetermined or previously determined altitude from the memory 118. The predetermined altitude may be calculated by the altitude estimation unit 402 during a previous test, e.g., an initialization procedure test, which had been previously stored in the memory 118. The previously determined altitude may represent an estimation of the altitude of the apparatus 100 that has been deemed plausible or acceptable. Alternatively, the predetermined altitude may be a reading obtained from the altimeter 112. The reading may also represent an accurate estimation of the altitude of the apparatus 100.

With continued reference to FIG. 7, the process at 704-708 may be identical to the process at 510-514 of FIG. 5, in which the altitude estimation unit 402 reads measurements from the pressure sensor 104, the motor speed sensor 108, and, optionally, the temperature sensor 110, and calculates the altitude of the apparatus 100 based on these measurements and the functions or equations previously described.

Thereafter, at 710, the altitude validation unit 404 may compare the altitude calculated by the altitude estimation unit 402 at 708 to the predetermined altitude obtained at step 702. If the altitude calculated at 708 reasonably approximates the previously determined altitude of the apparatus 100, then the measurements based on which the altitude is calculated may be deemed correct, which may suggest that the pressure sensor 104 is accurate or continues to be suitable for normal operation of the apparatus 100. For instance, if the difference between the calculated altitude and the predetermined altitude does not exceed a predetermined amount or threshold, e.g., 400 feet, 500 feet, 600 feet, 700 feet, 800 feet or 900 feet, then the pressure sensor 104 may be deemed suitable or accurate. As a result, the altitude validation unit 404 may, at 714, output a signal indicating that the pressure sensor 104 is accurate.

However, if the altitude calculated at 708 does not reasonably approximate the previously determined altitude of the apparatus 100, then the pressure sensor 104 may be deemed faulty. For instance, if the difference between the calculated altitude and the predetermined altitude exceeds a predetermined threshold, e.g., 400 feet, 500 feet, 600 feet, 700 feet, 800 feet or 900 feet, the pressure sensor 104 may be deemed inaccurate. The altitude validation unit 404 may, at 716, output a signal indicating that the pressure sensor 104 is inaccurate.

The periodic test procedure illustrated in FIG. 7 may assess the pressure sensor 104 using one cycle of analysis, which includes one instance of each of the following: taking a pressure measurement using the pressure sensor 104, taking a motor speed measurement using the motor speed sensor 108, optionally taking a temperature measurement using the temperature sensor 110, and calculating and evaluating the altitude based on these measurements. Such a periodic test procedure may optionally be implemented on a frequency of 1-10 hertz, such as 1, 2, 3, 4, 5, 6, 7, 8, 9 or 10 hertz sampling rate.

Figure 8:
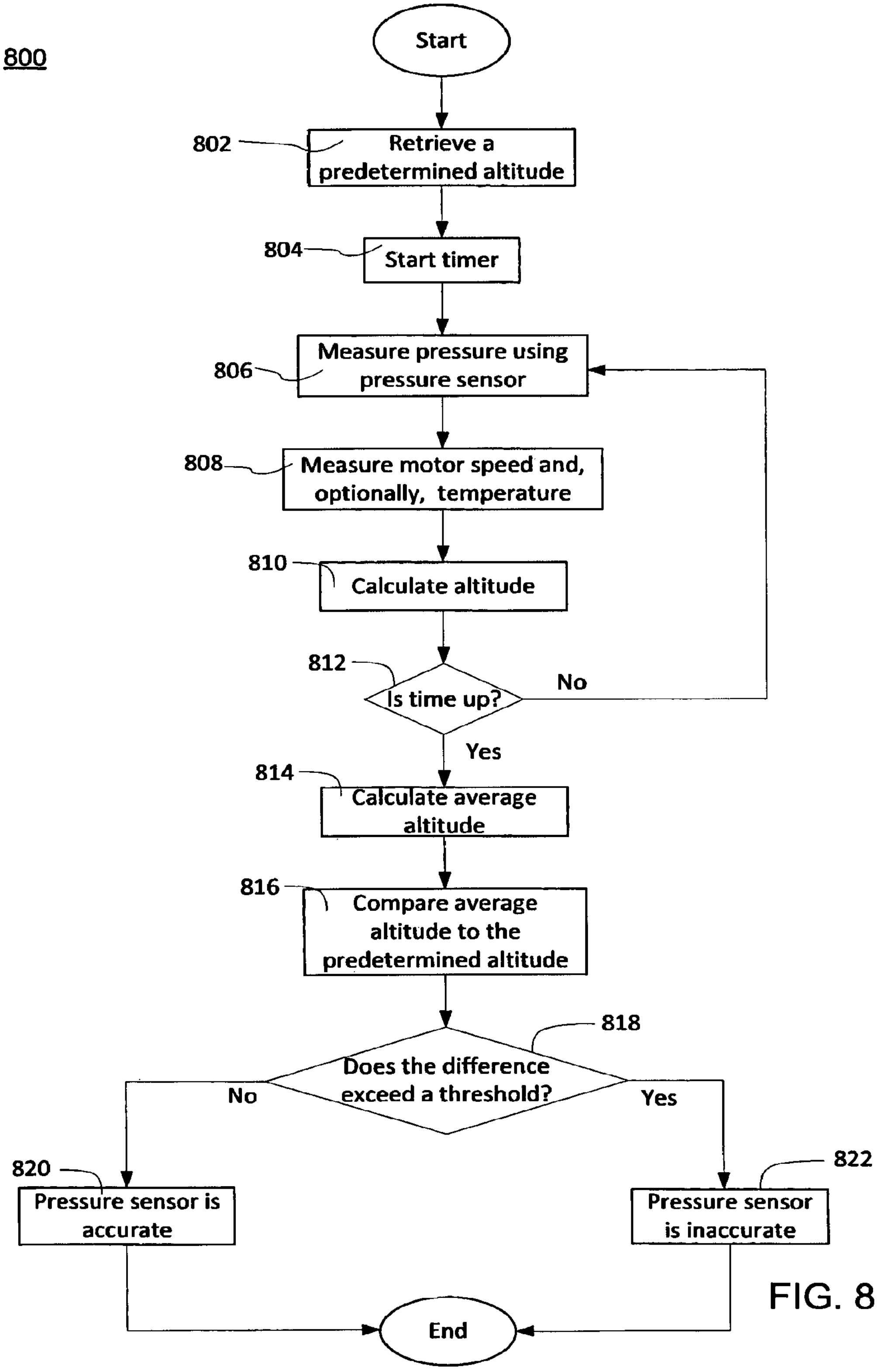
FIG. 8 is a flow diagram illustrating a method for determining accuracy of the pressure sensor according to still yet another embodiment.

FIG. 8 illustrates an alternate flow chart 800 embodiment to the periodic test procedure illustrated in FIG. 7. In this embodiment, the detector 120 may take a fault-tolerant approach to assess accuracy of the pressure sensor 104 based on averages. For instance, the detector 120 may determine accuracy of the pressure sensor 104 based on a collective result or average of multiple cycles of analysis. Each cycle of analysis may occur at a predetermined frequency, e.g., between 1 and 10 hertz, such as 1, 2, 3, 4, 5, 6, 7, 8, 9 or 10 hertz sampling rate.

As shown in FIG. 8, the processing at 802 may be identical to the processing at 702. At 804, the detector 120 may start a timer for the multiple cycles of analysis. Subsequently, the altitude estimation unit 402 may perform the processing at 806-810, which may be identical to the processing at 704-708 of FIG. 7. An iteration of the processing at 806-810 may be considered as one cycle of analysis. The altitude estimation unit 402 may repeatedly iterate the processing at 806-810 to perform multiple cycles of analysis, until a predetermined amount of time, e.g., 5, 10, 15, 20 or 30 seconds or longer or shorter periods of time, has elapsed since the start of the timer as determined at 812.

Thereafter, at 814, the altitude estimation unit 402 may calculate an average of the altitudes calculated during the multiple cycles of analysis or an altitude of average measurements from the multiple cycles. The altitude estimation unit 402 may output the average to the altitude validation unit 404.

Then, at 816-822, the altitude validation unit 404 may determine accuracy of the pressure sensor 104 based on analysis of the average altitude. In this regard, the processing at 816-822 may be identical to the processing at 710-716 of FIG. 7.

In a further embodiment, the timer 804 may be replaced with a counter configured to count the number of cycles and step 812 may determine if the desired number of cycles have been performed. In such an arrangement the detector 120 may assess accuracy of the pressure sensor 104 based on a predetermined number of cycles of analysis, e.g., at least 2 cycles of analysis or 5-10 cycles of analysis or more. The predetermined number of cycles may or may not be consecutive. For instance, the detector 120 may conclude that the pressure sensor 104 is inaccurate when the difference between the calculated altitude and the previously determined altitude exceeds the threshold amount in each of the at least 2 or 5-10 consecutive cycles of analysis. Alternatively, the detector 120 may concluded that the pressure sensor 104 is inaccurate when an average altitude calculated from the at least 2 or 5-10 cycles of analysis differs from the previously determined altitude by an offset greater than the predetermined threshold.

Figure 9:
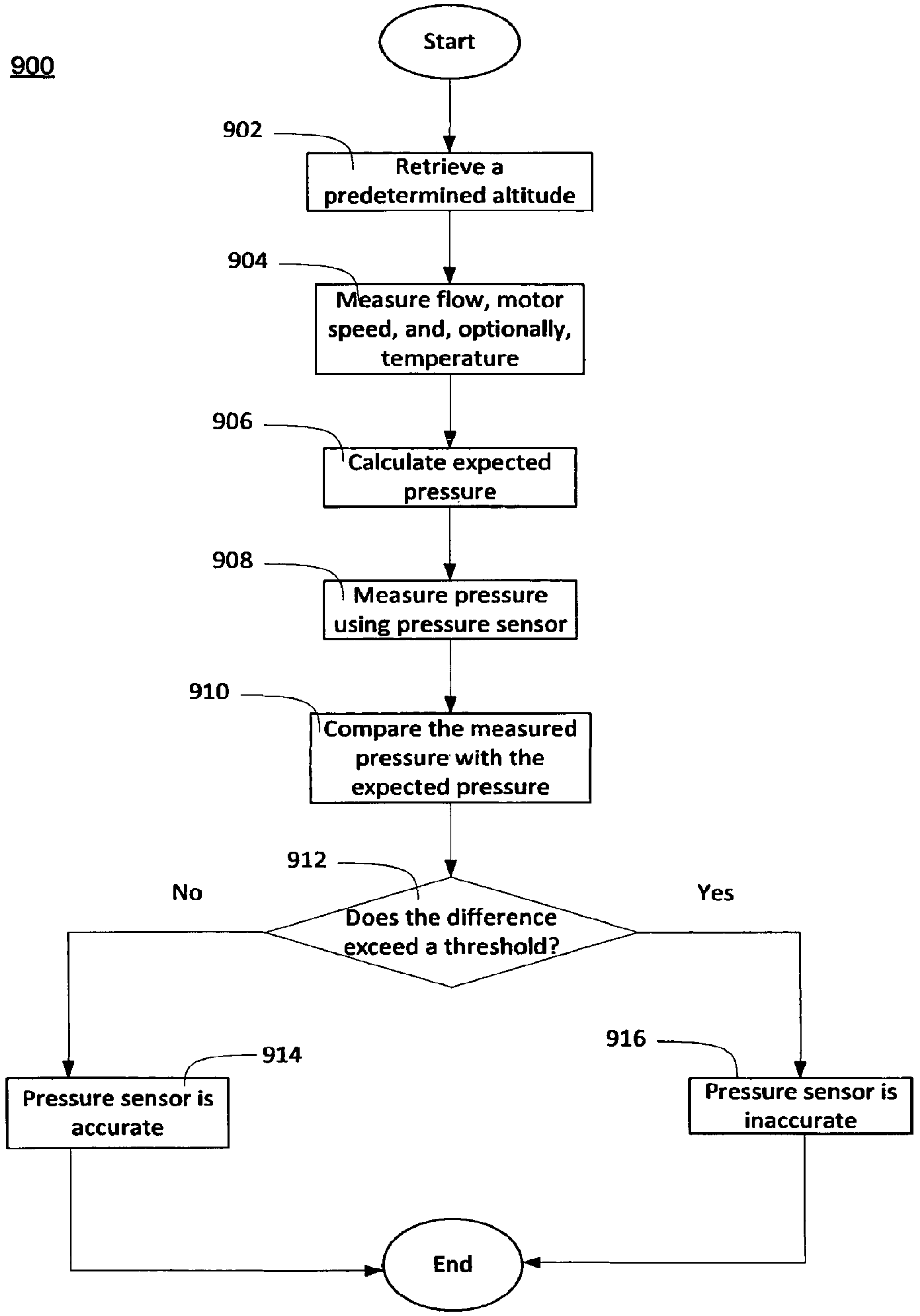
FIG. 9 is a flow diagram illustrating a method for determining accuracy of the pressure sensor according to a further embodiment.

FIG. 9 includes a flowchart 900 of a periodic test procedure according to another embodiment. At 902, the detector 120 may retrieve a previously determined altitude of the apparatus 100. Thus, the processing at 902 may be identical to the processing at 702 or 802 of FIGS. 7 and 8 respectively. At 904, the detector 120 or the pressure estimation unit 406 may obtain measurements from the flow sensor 106, the motor speed sensor 108, and, optionally, the temperature sensor 110. Thereafter, at 906, the pressure estimation unit 406 may calculate an expected pressure based on the predetermined altitude and the flow, motor speed and/or temperature measurements at 904 such as by the function previously mentioned (e.g., function B1 or a look-up table based thereon).

Then, at 908-910, the pressure validation unit 408 may obtain pressure measurement from the pressure sensor 104, and compare the measured pressure to the expected pressure. At 912, if the difference between the measured pressure and the expected pressure is equal to or less than a predetermined threshold, e.g., 5 $cmH_2O$, the pressure sensor 104 may be deemed accurate. Then, at 914, the pressure validation unit 408 may output a signal indicating that the pressure sensor 104 is accurate. As noted above the predetermined threshold may include other limits such as 1 cm $H_2O$, 2 $cmH_2O$, 3 $cmH_2O$, 4 $cmH_2O$, or 6 $cmH_2O$ or similar such limits.

By contrast, if the difference between the measured pressure and the expected pressure exceeds the predetermined threshold, the pressure sensor 104 may be deemed inaccurate. Then, at 916, the pressure validation unit 408 may output a signal indicating that the pressure sensor 104 is not suitable for normal operation.

Figure 10:
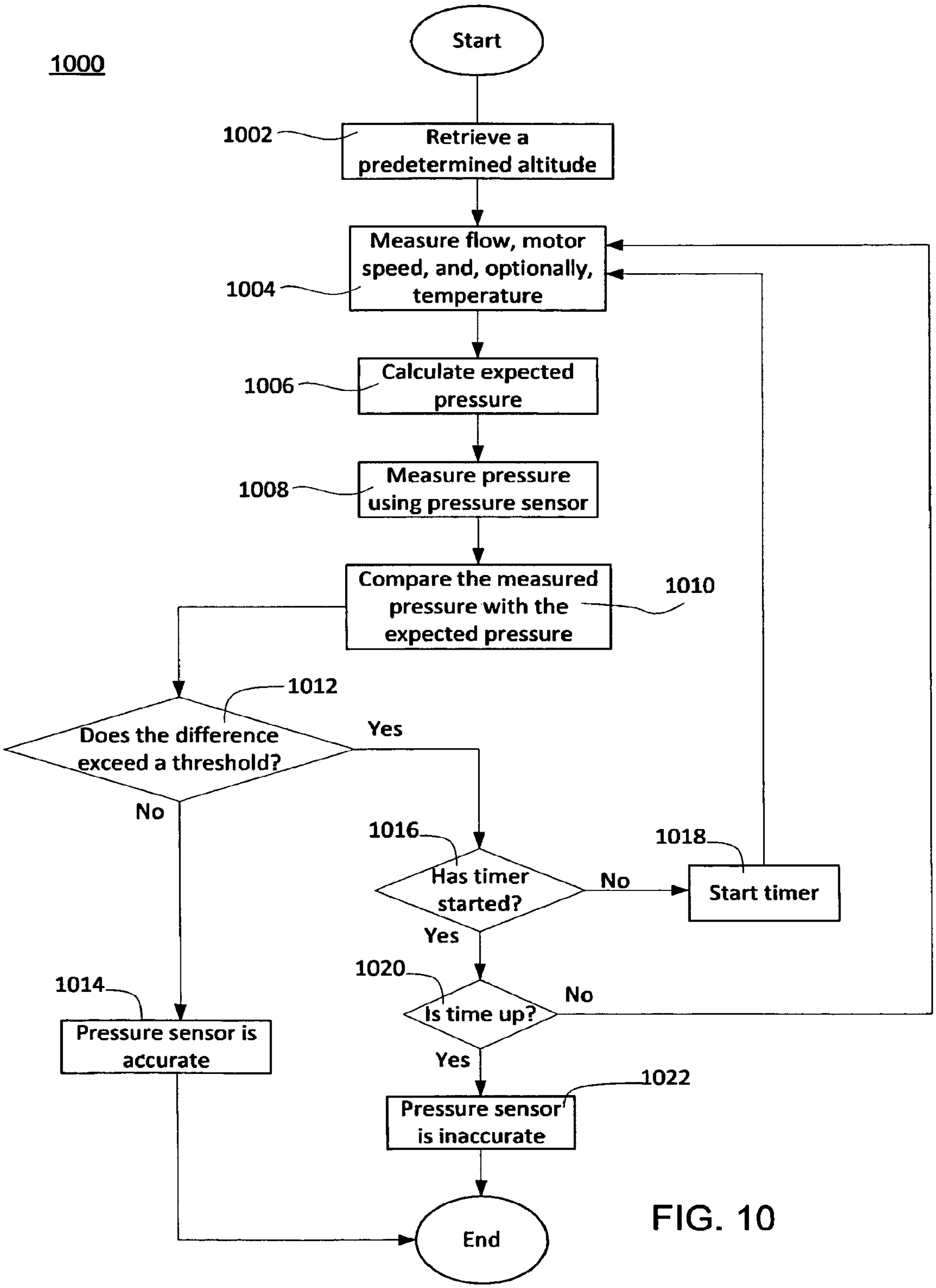
FIG. 10 is a flow diagram illustrating a method for determining accuracy of the pressure sensor according to a yet further embodiment.

FIG. 10 illustrates an alternate flow chart 1000 embodiment to the test procedure illustrated in FIG. 9. In this embodiment, the detector 120 may take a fault-tolerant approach to assess accuracy of the pressure sensor 104 based on multiple cycles of analysis over a predetermined period of time. The predetermined period of time may be, for example, 5, 10, 15, 20 or 30 seconds or longer or shorter periods of time. The detector 120 may include a timer or other iterative procedure to implement the repeated cycles of analysis. Each cycle of analysis may occur at a predetermined frequency, e.g., between 1 and 10 hertz, such as 1, 2, 3, 4, 5, 6, 7, 8, 9 or 10 hertz. Each cycle of analysis may include measuring flow, motor speed, and optionally, temperature, calculating expected pressure based on these measurements, comparing a reading of the pressure sensor 104 to the expected pressure. The pressure sensor 104 may be determined inaccurate or not suitable for normal operation when each pressure measurement differs from the expected pressure by an offset exceeding a threshold amount, e.g., 5 $cmH_2O$, over a predetermined period of time.

As shown in FIG. 10, the processing at 1002-1014 may be identical to the processing at 902-914 of FIG. 9. An iteration of the processing at 1004-1012 may be considered as one cycle of analysis. The detector 120 may repeatedly iterate steps 1004-1012 to perform multiple cycles of analysis. If the measured pressure differs from the expected pressure by an offset greater than a threshold amount, e.g., 5 $cmH_2O$, at 1012, the detector 120 may proceed to 1016. At 1016, the detector 120 may determine whether a timer for the multiple cycles of analysis has started. If the timer has not started, the detector 120 may start the timer at 1018, and may then proceed to 1004 to start a new cycle of analysis. If the timer has already started, then the detector 120 may, at 1020, determine whether the predetermined amount of time, e.g., 5, 10, 15, 20 or 30 seconds, has elapsed since the start of the timer. If not, the detector 120 may proceed to 1004 to start a new cycle of analysis. If yes, the detector 120 may proceed to 1022 to output a signal indicating that the pressure sensor 104 is inaccurate. At that point, the detector 120 may optionally stop or reset the timer. As noted above the predetermined threshold may include other limits such as 1 cm $H_2O$, 2 $cmH_2O$, 3 $cmH_2O$, 4 $cmH_2O$, or 6 $cmH_2O$ or similar such limits.

If during any cycle of analysis, the difference between the measured pressure and the expected pressure does not exceed the predetermined threshold at 1012, the detector 120 may, at 1014, output a signal indicating that the pressure sensor 104 is accurate or suitable for normal operation.

In a further embodiment, the timer 1018 may be replaced with a counter configured to count the number of cycles and step 1020 may determine if the desired number of cycles have been performed. In such an arrangement the detector 120 may assess accuracy of the pressure sensor 104 based on a predetermined number of cycles of analysis, e.g., 10 cycles of analysis. The predetermined number of cycles may or may not be consecutive. For instance, the detector 120 may conclude that the pressure sensor 104 is inaccurate when the difference between the calculated altitude and the predetermined altitude exceeds the threshold amount (e.g., $((|P_{meas}-P_{est}|)>5\ cmH_2O))$ in each of the 10 consecutive cycles of analysis.

In some embodiments, the detector 120 may perform an initial test of the pressure sensor 104 according to the steps described in FIG. 5 or FIG. 6 before the apparatus 100 provides therapeutic treatment to a patient. The detector 120 may continuously monitor the accuracy of the pressure sensor 104 in one or more periodic tests as the apparatus 100 provides therapeutic treatment to the patient according to procedures described in any one of FIGS. 7-10. In one embodiment, the predetermined altitude retrieved at one of the steps 702, 802, 902 and 1002 may be an altitude calculated by the altitude estimation unit 402 in the initial test. In another embodiment, the predetermined altitude may be a reading obtained from the altimeter 122. Alternatively, the predetermined altitude may be a range of expected altitudes, examples of which are described previously.

In another embodiment, an initial test may be implemented using procedures described in any one of FIGS. 7-10. In this embodiment, the predetermined altitude retrieved at any one of the processes 702, 802, 902 and 1002 may be an altitude calculated by the altitude estimation unit 402 in a previous test related to a previous therapeutic treatment. Alternatively, the predetermined altitude may be a reading obtained from the altimeter 122. The predetermined altitude may also represent a range of expected altitudes that the apparatus 100 may operate.

In a further embodiment, the detector 120 may constantly test the accuracy of the pressure sensor 104 by executing procedures described in any one of FIGS. 5-10 at a predetermined interval before and throughout the therapeutic treatment to the patient.

Dual Pressure Sensors

While the examples previously described herein permit evaluation of a measurement of a pressure sensor without implementing a second pressure sensor and in some cases without an altimeter, in some alternative embodiments, measurements of a second or back-up pressure sensor may be implemented to check the pressure of a first pressure sensor. For example, the apparatus 100 may optionally include a second pressure sensor 124 as illustrated in FIG. 1. The second pressure sensor 124 may be positioned in a close proximity to the first pressure sensor 104, such that both pressure sensors 104, 124 may measure pressure of the gas at the same location. For example, both pressure sensors 104, 124 may be positioned at the patient interface 132 or at the blower 130. If the first pressure measurement differs from the second pressure measurement by an offset greater than a predetermined threshold, e.g., 5 $cmH_2O$, the first pressure sensor 104 may be deemed inaccurate. Otherwise, the first pressure sensor 104 may be deemed accurate.

Alternatively the second pressure sensor 1124 may be positioned at a different location to the first pressure sensor 104, such as the first pressure sensor 104 may be positioned at the patient interface 132 and the second pressure sensor 124 positioned at the blower 130 or vice versa. The pressure drop between the two pressure sensors may be known, estimated or characterized such that the pressure drop between the pressure sensors is taken into consideration when comparing the pressure measurements obtained from the first pressure sensor 104 and the second pressure sensor 124. Thus the difference between the pressure measurements from first pressure sensor 104 and the second pressure sensor 124 may not exceed a predetermined threshold that is determined as a function of the pressure drop between the first pressure sensor 104 and the second pressure sensor 124.

Figure 11:
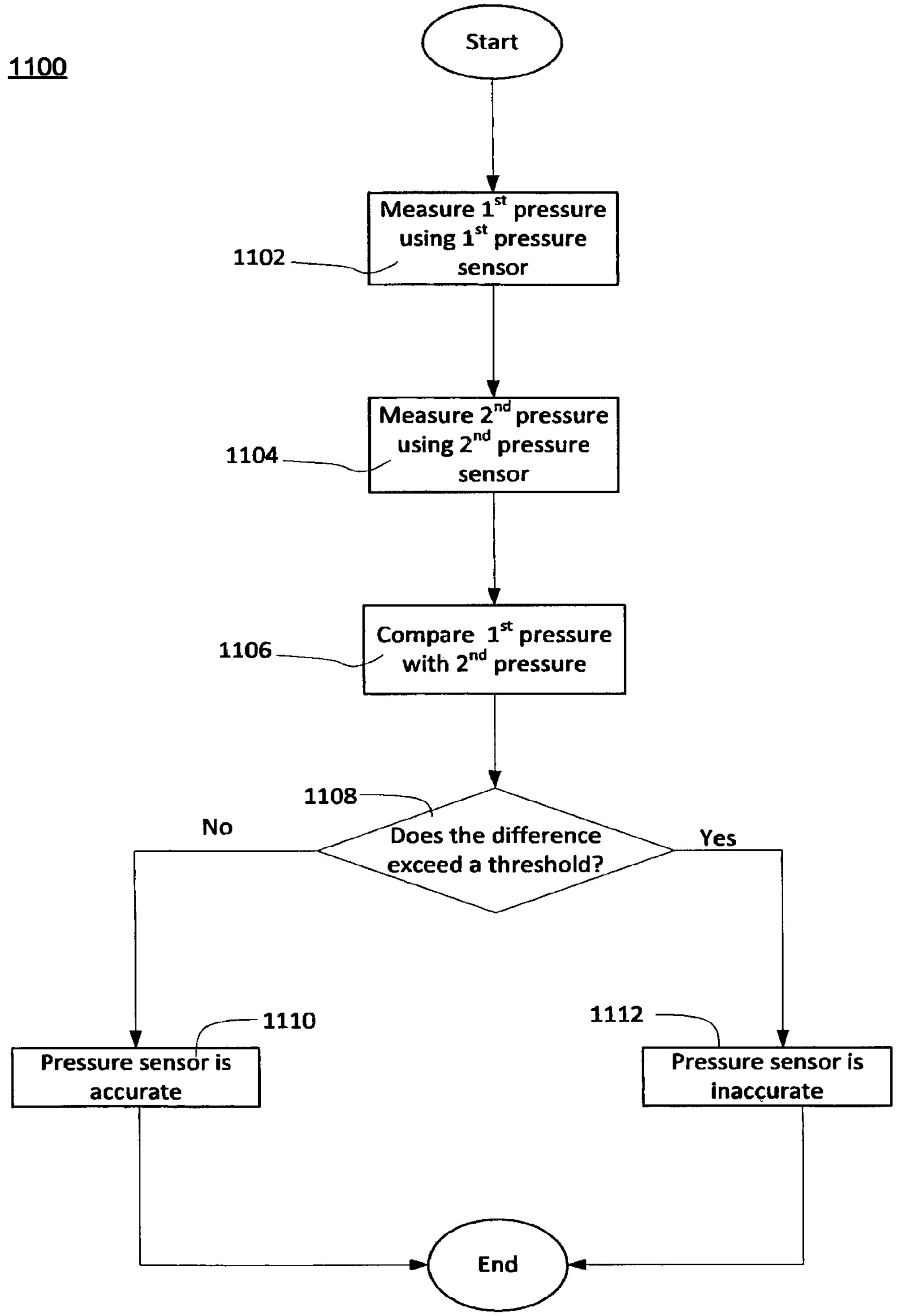
FIG. 11 is a flow diagram illustrating a method for determining accuracy of the pressure sensor according to a still yet further embodiment.

FIG. 11 illustrates a flowchart 1100 of a method performed by the detector 120 according to the above embodiment. At 1102, the detector 120 may obtain a first pressure measurement from the first pressure sensor 104. At 1104, the detector 120 may obtain a second pressure measurement from the second pressure sensor 124. At 1106, the detector 120 may compare the first pressure measurement to the second pressure measurement. Thereafter, at 1108, the detector 120 may determine if the first pressure measurement differs from the second pressure measurement by an offset greater than a threshold amount, e.g., 5 $cmH_2O$. If no, the detector 120 may at 1110 issue a signal indicating that the first pressure sensor 104 is accurate. If yes, the detector 120 may, at 1112, issue a signal indicating that the first pressure sensor 104 is inaccurate.

As noted above the predetermined threshold may include other limits such as 1 cm $H_2O$, 2 $cmH_2O$, 3 $cmH_2O$, 4 $cmH_2O$, or 6 $cmH_2O$ or similar such limits.

Response to Faulty Sensor Detection

If the detector 120 determines that the pressure sensor 104 is inaccurate or not suitable for normal operation, then a fault has been detected in the pressure sensor 104.

In the absence of such a fault, the apparatus 100 may operate normally (e.g., with a pressure control loop that relies on the pressure measurements from the pressure sensor 104 for control of the blower 130 and the patient's treatment).

In the detection of a fault, the apparatus 100 may respond with an automatic shutdown to prevent further execution. Alternatively, the apparatus 100 may record data of the fault and/or issue a warning or a fault message to the user via the user I/O devices 114. For instance, a display (not shown) may display a message to the user that the pressure sensor 104 is inaccurate and needs to be replaced. In such a case, the controller, e.g., the processor 116, may be configured to prevent operation of the blower 130.

In some embodiments, the apparatus 100 may include a pressure sensor fault handler 122 to control the apparatus 100, once a fault has been detected in the pressure sensor 104. In these embodiments, the apparatus 100 may optionally be permitted to operate in a safe mode, despite the detection of a fault. For example, the handler 122 may include two alternate operational safe modes: a pressure-controlled, speed limited mode or a speed-controlled mode, in which the apparatus 100 may operate. The handler 122 may enter either one of the operational modes once the pressure sensor 104 is determined to not be suitable for normal operation.

In the pressure-controlled, speed limited mode, the handler 122 may adjust the motor speed of the flow generator 102 by relying on the pressure measurement by the pressure sensor 104 (e.g., controlling the blower 130 using a pressure control loop), irrespective of the fact that pressure sensor 104 is deemed inaccurate. More specifically, the handler 122 may increase the motor speed until the measured pressure from the pressure sensor 104 reaches a desired pressure level, but in no event, may the motor speed exceed a predetermined maximum motor speed. In such a case, a maximum motor speed limit will act to override a pressure demand from the pressure control loop to prevent further increase in the motor speed beyond the limit despite a pressure set point falling short of the measured pressure from the pressure sensor 104.

Figure 12:
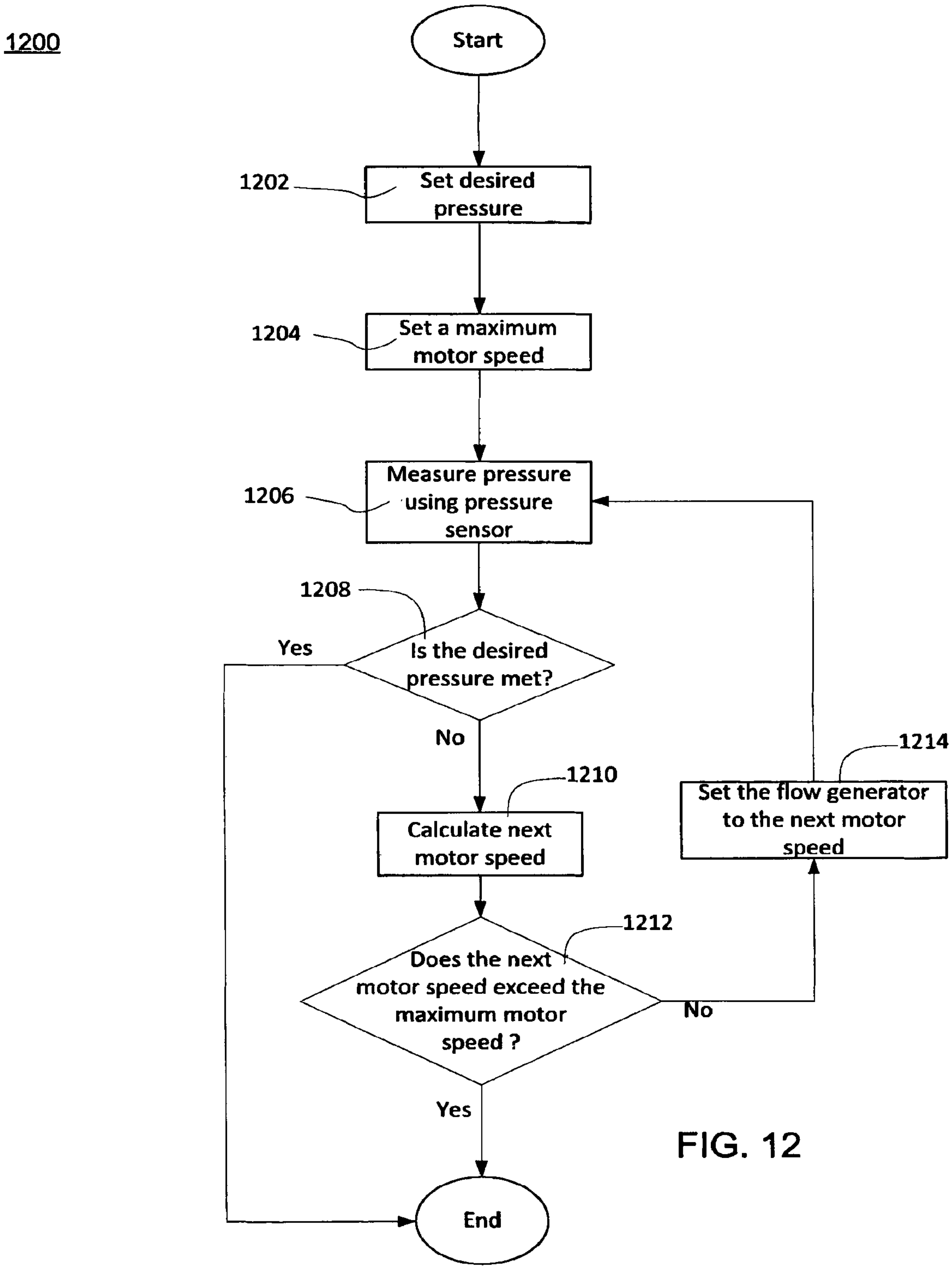
FIG. 12 is a flow diagram of a method by a pressure sensor fault handler according to one embodiment.

FIG. 12 illustrates a flowchart 1200 describing operations of the handler 122 in the pressure-controlled mode according to one embodiment. At 1202, the handler 122 may determine a desired pressure level setting for the gas to be achieved with the flow generator 102. The desired pressure level may be the desired therapeutic treatment pressure to be applied to the patient. In one example, the desired pressure level may be manually entered by the user via the user I/O devices 114. In another example, the processor 114 or the handler 122 may calculate the desired pressure level based on the condition of the patient. The desired pressure level may be a constant pressure value expected to be maintained throughout one therapeutic treatment session. Alternatively, the desired pressure level may vary throughout one therapeutic treatment session. For instance, during one therapeutic treatment session, the desired pressure level during inhalation may be greater than the desired pressure level during exhalation. Additionally, the desired pressure level may be automatically adjusted and determined based on detected breathing conditions (e.g., obstructive apnea, obstructive hypopnea, flow limitation, snoring, other sleep disordered breathing events, etc.).

At 1204, the handler 122 may set a motor speed threshold. The motor speed threshold may represent a maximum motor speed that the flow generator 102 is allowed to attain, above which the flow generator 102 or other components of the apparatus 100 may deteriorate or malfunction or may be deemed dangerous for a patient. In one example, the handler 122 may set the motor speed threshold to an RPM threshold, such as 20,000 RPM, 30,000, RPM, 50,000 RPM, 100,000 RPM, 200,000 RPM or other suitable speeds. The RPM threshold may be determined based on an approximate expected motor speed required to meet the desired pressure or a maximum pressure from previous system characterization, and may, for example, be obtained from a look-up table of the memory of the apparatus.

At 1206, the handler 122 may obtain a pressure reading from the pressure sensor 104. At 1208, the handler 122 may compare the measured pressure to the desired pressure level. If the measured pressure reaches the desired pressure level, the handler 122 may terminate the adjustment operation. Otherwise, the handler 122 may, at 1210, change the next motor speed for the flow generator 102. In one example, the next motor speed may be increased from the present motor speed by a predetermined increment. Thereafter, at 1212, the handler 122 may determine if the next motor speed exceeds the motor speed threshold. If yes, the handler 122 may terminate the adjustment operation. If not, the handler 122 may, at 1214, instruct the flow generator 102 to change from its present motor speed to the next motor speed. Thereafter, the handler 122 may proceed to 1206 to measure pressure using the pressure sensor 104.

In the speed-controlled mode, the apparatus 100 may no longer operate by a pressure control loop but may operate in a speed control loop. In such a mode, the handler 122 may determine a desired motor speed of the flow generator 102 that correlates to the desired pressure level (such as with a look-up table or suitable function to relate pressure to a motor speed setting), such that when the flow generator 102 operates at the desired motor speed, the gas generated by the flow generator 102 may be deemed to be at the desired pressure level. Thus, in the speed-controlled mode, the handler 122 may determine the desired motor speed without taking into consideration the pressure measurement obtained from the pressure sensor 104. In one example, the handler 122 may include a look-up table that defines a correlation between a plurality of different motor speeds and a plurality of different pressure levels. The look-up table may define one-on-one mappings between the plurality of different motor speeds and the plurality of different pressure levels. Once a desired pressure level is determined, the handler 122 may look up its corresponding motor speed, i.e., the desired motor speed, in the look-up table. The handler 122 may then set the flow generator 102 to the desired motor speed.

Figure 13:
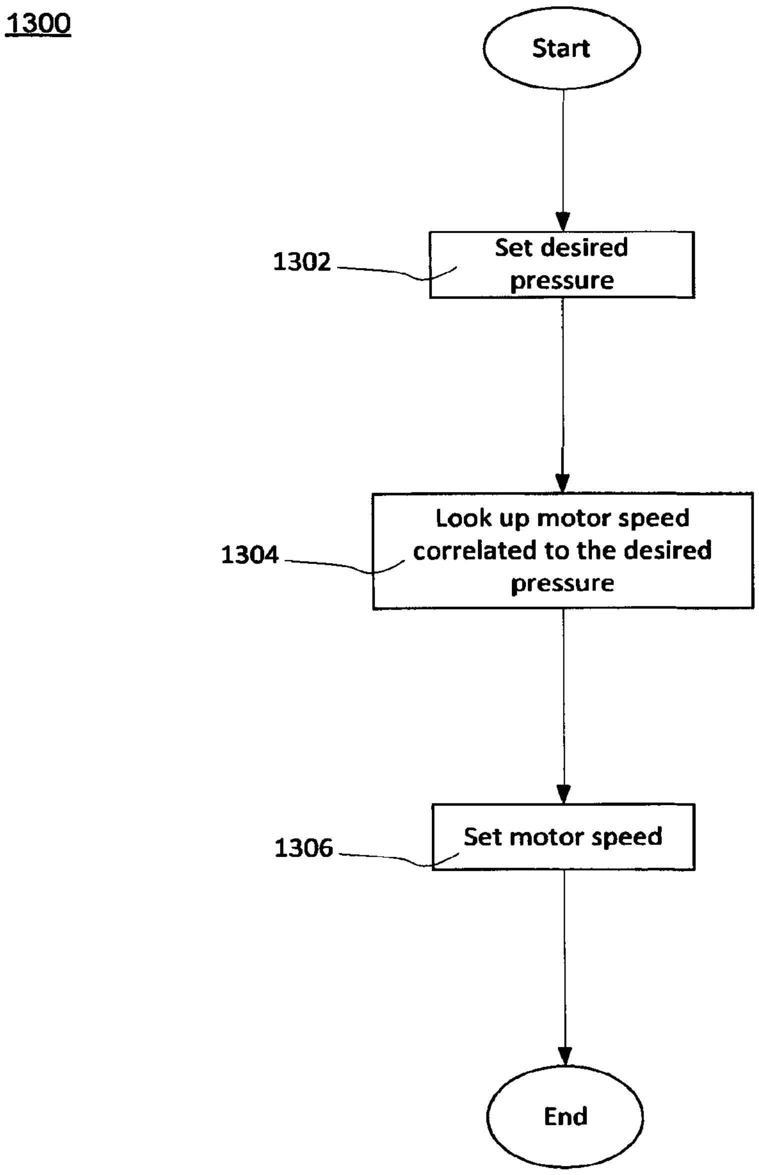
FIG. 13 is a flow diagram of a method by a pressure sensor fault handler according to another embodiment.

FIG. 13 illustrates a flowchart 1300 describing operations of the handler 122 in the speed-controlled mode according to one embodiment. At 1302, the handler 122 may determine a desired pressure level to be set. The processing at 1302 may be identical to the processing at 1202. At 1304, the handler 122 may look up a desired motor speed correlated to the desired pressure level in the look-up table. At 1306, the handler 122 may servo-control the flow generator 102 to the desired motor speed in a speed control loop.

Although the invention herein has been described with reference to particular embodiments, it is to be understood that these embodiments are merely illustrative of the principles and applications of the present technology. It is therefore to be understood that numerous modifications may be made to the illustrative embodiments and that other arrangements may be devised without departing from the spirit and scope of the present technology.

For example, although versions of the technology described herein have generally referred to a determination, estimation or measurement of altitude in its methodologies such that the altitude (or elevation) is serving as a subordinate or secondary characteristic of the respiratory treatment apparatus that may be derived from pressure and/or from which pressure is derivable by some calculable function(s) that may involve some measured system variable(s), it will be understood that some versions of the present technology may alternatively implement components that make a determination, estimation or measurement of some other such subordinate or secondary characteristic rather than altitude in any of the previously described methodologies.

For example, in some such versions, the detector 120 may obtain a pressure measure from the pressure sensor 104. The detector 120 may evaluate accuracy of the pressure sensor 104 based on the pressure measure and a subordinate or secondary characteristic, such as atmospheric pressure or the atmospheric pressure external to the apparatus 100. Such atmospheric pressure of the apparatus 100 may include one or more of (1) a previously calculated atmospheric pressure estimate from a prior pressure measure of the apparatus 100 (e.g., a pressure measure in the flow path of the apparatus which generating a pressure above atmospheric pressure), (2) an expected atmospheric pressure or atmospheric pressure range for the apparatus 100, (3) an actual or expected atmospheric pressure input into the apparatus 100 for operation; and/or (4) an atmospheric pressure measured by an external sensor of the apparatus 100 such as a barometer. The detector 120 may calculate an atmospheric pressure estimate based on the pressure measure, and compare the atmospheric pressure estimate to any one or more of the atmospheric pressure (1)-(4) described above. Still other secondary characteristics may also be implemented in any of the methodologies described herein.

For example, in the case of the subordinate characteristic being atmospheric pressure, the altitude estimation unit 402 may instead be an atmospheric pressure estimation unit. Thus it may calculate an estimate of the atmospheric pressure during operation of the apparatus 100 as a function of some or all of the following: the measured pressure of the gas obtained from the pressure sensor 104, the measured flow rate of the gas obtained the flow sensor 106, the measured temperature obtained from the temperature sensor 110, and the measured motor speed obtained from the motor speed sensor 108. For example, an atmospheric pressure estimation unit may compute the atmospheric pressure of the apparatus 100 according to the following function:

$$Atm=f_x(P,Q,T \text{ and } \omega)$$

where:

Atm is the estimated atmospheric pressure;

P is the measure of pressure;

Q is a measure of flow;

T is an optional measure of temperature that in some embodiments may be omitted; and ω is a measure of motor speed.

$f_x$ may be a polynomial function (e.g., $y=Ax^2+Bx+c$ of a suitable degree depending on the constants and parameters of the function) applied to the measured values that may be derived empirically, such as by a Gray Box Model or best fit model using suitable test data. Other such functions may be implemented similar to those previously described with reference to altitude. Similarly, the altitude validation unit 404 may be implemented as an atmospheric pressure validation unit.

ADDITIONAL TECHNOLOGY EXAMPLES

Example 1. A method for determining accuracy of a pressure sensor in a respiratory device, comprising:

measuring pressure of a flow of breathable gas generated by the respiratory device using the pressure sensor; and determining, with a processor, accuracy of the pressure sensor based on the measured pressure and a subordinate characteristic of the respiratory device.

Example 2. The method of Example 1, wherein the respiratory device includes a flow generator with a motor included therein to generate the flow of gas.

Example 3. The method of any one of Examples 1-2, wherein the subordinate characteristic of the respiratory device is input by a user.

Example 4. The method of any one of Examples 1-2, wherein the subordinate characteristic of the respiratory device is measured by an altimeter or barometer of the respiratory device.

Example 5. The method of any one of Examples 1-4, wherein the processor calculates the subordinate characteristic of the respiratory device.

Example 6. The method of Example 5, wherein the processor determines the accuracy of the pressure sensor based on an evaluation of the calculated subordinate characteristic.

Example 7. The method of any one of Examples 5-6, wherein the processor calculates the subordinate characteristic of the respiratory device as a function of (a) the pressure measured by the pressure sensor and one or both of (b)(1) a measured flow rate of the flow of breathable gas and (b)(2) a measured motor speed of the flow generator.

Example 8. The method of Example 7, wherein the processor calculates the subordinate characteristic of the respiratory device as a function of a measured temperature of the flow of breathable gas.

Example 9. The method of any one of Example 5-8, wherein the processor calculates the subordinate characteristic of the respiratory device when the flow generator controls the gas at a constant predetermined flow rate.

Example 10. The method of Example 9, wherein the constant predetermined flow rate is 20 liters/minute.

Example 11. The method of Example 9, wherein the constant predetermined flow rate is less than 50 liters/minute.

Example 12. The method of Example 9, wherein the constant predetermined flow rate is in the range between about 10 liters/minute and about 60 liters/minute.

Example 13. The method of any one of Examples 5-8, wherein the subordinate characteristic of the respiratory device is calculated when the flow generator controls a constant predetermined motor speed.

Example 14. The method of any one of Examples 6-13, wherein the processor evaluates the calculated subordinate characteristic by comparing the calculated subordinate characteristic with a predetermined range of the subordinate characteristic.

Example 15. The method of Example 14, wherein the predetermined range of the subordinate characteristic corresponds to a range between 0 and 9000 feet above sea level.

Example 16. The method of Example 14, wherein the predetermined range of the subordinate characteristic corresponds to a range between 500 feet below sea level and 10,000 feet above sea level.

Example 17. The method of any one of Examples 14-16, wherein the processor deems the calculated subordinate characteristic acceptable when the calculated subordinate characteristic is within the predetermined range of the subordinate characteristic.

Example 18. The method of any one of Examples 14-17, wherein the processor deems the calculated subordinate characteristic unacceptable when the calculated subordinate characteristic is outside the predetermined range of the subordinate characteristic.

Example 19. The method of any one of Examples 5-18, wherein the processor calculates the subordinate characteristic of the respiratory device at a predetermined frequency over a predetermined period of time.

Example 20. The method of Example 19, wherein the predetermined frequency is between 1 and 2 hertz.

Example 21. The method of any one of Examples 19-20, wherein the predetermined period of time is 5 seconds.

Example 22. The method of any one of Examples 19-21, wherein the processor evaluates the pressure sensor based on an average of the calculated subordinate characteristic.

Example 23. The method of any one of Examples 19-22, wherein the processor determines the pressure sensor accurate when an average of the calculated subordinate characteristic satisfies a threshold comparison.

Example 24. The method of any one of the preceding Examples, wherein the processor evaluates the pressure sensor in an initialization process before the respiratory device provides treatment to a patient.

Example 25. The method of any one of the preceding Examples, further comprising storing the subordinate characteristic of the respiratory device in a memory.

Example 26. The method of any one of Examples 2-25, wherein the processor evaluates accuracy of the pressure sensor by:

calculating expected pressure of the gas generated by the respiratory device; and comparing the measured pressure with the expected pressure.

Example 27. The method of Example 26, wherein the processor calculates the expected pressure from the subordinate characteristic of the respiratory device, a measured flow rate of the flow of breathable gas, and a measured motor speed of the flow generator.

Example 28. The method of Example 27, wherein the processor calculates the expected pressure from a measured temperature of the flow of breathable gas.

Example 29. The method of any one of Examples 26-28, wherein the processor determines the accuracy of the pressure sensor by comparing a difference between the measured pressure and the expected pressure with a predetermined threshold.

Example 30. The method of Example 29, wherein the predetermined threshold is 5 $cmH_2O$.

Example 31. The method of any one of Examples 29-30, wherein the processor determines the pressure sensor inaccurate when the difference exceeds the predetermined threshold.

Example 32. The method of any one of Examples 29-31, wherein the processor determines the pressure sensor accurate when the difference is within the predetermined threshold.

Example 33. The method of any one of Examples 26-32, wherein the measurement of the pressure, the calculation of the expected pressure, and the comparison of the measured pressure with the expected pressure are performed at a predetermined frequency over a predetermined period of time.

Example 34. The method of Example 33, wherein the predetermined frequency is between 1 and 2 hertz.

Example 35. The method of any one of Examples 33-34, wherein the predetermined period of time is 5 seconds.

Example 36. The method of any one of Examples 33-35, wherein the processor determines the pressure sensor inaccurate based on a plurality of comparisons between measured pressures and expected pressures.

Example 37. The method of any one of Examples 2-25, wherein the subordinate characteristic of the respiratory device is a first subordinate characteristic, and wherein the processor determines the accuracy of the pressure sensor by:

calculating a second subordinate characteristic of the respiratory device; and comparing the second subordinate characteristic of the respiratory device with the first subordinate characteristic of the respiratory device.

Example 38. The method of Example 37, wherein the processor calculates the second subordinate characteristic of the respiratory device from a measured flow rate of the flow of breathable gas, a measured motor speed of the flow generator, and the pressure measured by the pressure sensor.

Example 39. The method of Example 38, wherein the processor calculates the second subordinate characteristic of the respiratory device from a measured temperature of the flow of breathable gas.

Example 40. The method of any one of Examples 37-39, wherein the processor determines the accuracy of the pressure sensor by comparing a difference between the first subordinate characteristic and the second subordinate characteristic with a predetermined threshold.

Example 41. The method of Example 40, wherein the predetermined threshold corresponds with 600 feet.

Example 42. The method of any one of Examples 40-41, wherein the processor determines the pressure sensor inaccurate when the difference exceeds the predetermined threshold.

Example 43. The method of any one of Examples 40-42, wherein the processor determines the pressure sensor accurate when the difference is within the predetermined threshold.

Example 44. The method of any one of Examples 37-43, wherein the processor calculates the second subordinate characteristic at a predetermined frequency for a predetermined period of time.

Example 45. The method of Example 44, wherein the predetermined frequency is between 1 and 2 hertz.

Example 46. The method of any one of Examples 44-45, wherein the predetermined period of time is 5 seconds.

Example 47. The method of any one of Examples 44-46, wherein the processor determines the pressure sensor inaccurate when an average of the second subordinate characteristic calculated during the predetermined period of time differs from the first subordinate characteristic by an offset greater than a predetermined threshold.

Example 48. The method of any one of Examples 44-47, wherein the processor determines the pressure sensor accurate when an average of the second subordinate characteristic calculated during the predetermined period of time differs from the first subordinate characteristic by an offset not greater than a predetermined threshold.

Example 49. The method of any one of Examples 2-48, further comprising setting a motor speed for the flow generator based on the measured pressure, when the processor determines the pressure sensor inaccurate.

Example 50. The method of Example 49, further comprising maintaining the motor speed under a speed limit threshold.

Example 51. The method of any one of Examples 2-48, further comprising determining a desired gas pressure to be generated by the flow generator, and determining a desired motor speed for the flow generator based on a predetermined association between motor speed values and pressure values.

Example 52. A respiratory apparatus comprising:

a flow generator with a blower included therein to generate a flow of breathable gas for delivery to a patient interface at a pressure above atmospheric pressure;

a pressure sensor coupled with the flow generator, the pressure sensor configured to measure pressure of the flow of breathable gas; and a processor coupled with the pressure sensor configured to determine accuracy of the pressure sensor based on the measured pressure and an subordinate characteristic of the respiratory apparatus.

Example 53. The respiratory apparatus of Example 52, further comprising a flow sensor configured to measure a flow rate of the flow of breathable gas.

Example 54. The respiratory apparatus of any one of Examples 52-53, further comprising a motor speed sensor configured to measure a motor speed of the flow generator.

Example 55. The respiratory apparatus of any one of Examples 52-54, further comprising a user I/O device configured to receive the subordinate characteristic of the respiratory apparatus input by a user.

Example 56. The respiratory apparatus of any one of Examples 52-55, further comprising an altimeter or barometer to determine the subordinate characteristic of the respiratory apparatus.

Example 57. The respiratory apparatus of any one of Examples 52-56, wherein the processor is configured to calculate the subordinate characteristic of the respiratory apparatus.

Example 58. The respiratory apparatus of Example 57, wherein the processor determines accuracy of the pressure sensor based on evaluation of the calculated subordinate characteristic.

Example 59. The respiratory apparatus of any one of Examples 57-58, wherein the processor calculates the subordinate characteristic of the respiratory apparatus as a function of (a) the pressure measured by the pressure sensor and one or both of (b1) a measured flow rate of the flow of breathable gas and (b)(2) a measured motor speed of the flow generator.

Example 60. The respiratory apparatus of Example 59, wherein the processor calculates the subordinate characteristic of the respiratory apparatus as a function of a measured temperature of the flow of breathable gas.

Example 61. The respiratory apparatus of any one of Examples 57-60, wherein the processor calculates the subordinate characteristic of the respiratory apparatus when the flow generator controls the gas at a constant predetermined flow rate.

Example 62. The respiratory apparatus of Example 61, wherein the constant predetermined flow rate is 20 liters/minute.

Example 63. The respiratory apparatus of Example 61, wherein the constant predetermined flow rate is less than 50 liters/minute.

Example 64. The respiratory apparatus of Example 61, wherein the constant predetermined flow rate is in the range between about 10 liters/minute and about 60 liters/minute.

Example 65. The respiratory apparatus of any one of Examples 57-60, wherein the processor calculates the subordinate characteristic of the respiratory apparatus when the flow generator controls a constant predetermined motor speed.

Example 66. The respiratory apparatus of any one of Examples 58-65, wherein the processor evaluates the calculated subordinate characteristic by comparing the calculated subordinate characteristic with a predetermined range of the subordinate characteristic.

Example 67. The respiratory apparatus of Example 66, wherein the predetermined range of the subordinate characteristic is a range that corresponds with between 0 and 9000 feet above sea level.

Example 68. The respiratory apparatus of claim 66, wherein the predetermined range of the subordinate characteristic is a range that corresponds with between 500 feet below sea level and 10,000 feet above sea level.

Example 69. The respiratory apparatus of any one of Examples 66-68, wherein the processor deems the calculated subordinate characteristic acceptable when the calculated subordinate characteristic is within the predetermined range of the subordinate characteristic.

Example 70. The respiratory apparatus of any one of Examples 66-69, wherein the processor deems the calculated subordinate characteristic unacceptable when the calculated subordinate characteristic is outside the predetermined range of the subordinate characteristic.

Example 71. The respiratory apparatus of any one of Examples 57-70, wherein the processor calculates the subordinate characteristic of the respiratory apparatus at a predetermined frequency for a predetermined period of time.

Example 72. The respiratory apparatus of claim 71, wherein the predetermined frequency is between 1 and 2 hertz.

Example 73. The respiratory apparatus of any one of Examples 71-72, wherein the predetermined period of time is 5 seconds.

Example 74. The respiratory apparatus of any one of Examples 71-73, wherein the processor evaluates the pressure sensor based on an average of the calculated subordinate characteristic.

Example 75. The respiratory apparatus of any one of Examples 71-74, wherein the processor determines the pressure sensor accurate when an average of the calculated subordinate characteristic satisfies a threshold comparison.

Example 76. The respiratory apparatus of any one of Examples 52-75, wherein the processor evaluates the pressure sensor in an initialization process before the respiratory apparatus provides treatment to a patient.

Example 77. The respiratory apparatus of any one of Examples 52-76, further comprising a memory to store the subordinate characteristic of the respiratory apparatus.

Example 78. The respiratory apparatus of any one of Examples 52-77, wherein the processor evaluates accuracy of the pressure sensor by:

calculating expected pressure of the gas generated by the respiratory apparatus; and comparing the expected pressure with the pressure measured by the pressure sensor.

Example 79. The respiratory apparatus of Example 78, wherein the processor calculates the expected pressure using the subordinate characteristic of the respiratory apparatus, a measured flow rate of the flow of breathable gas, and a measured motor speed of the flow generator.

Example 80. The respiratory apparatus of Example 79, wherein the processor calculates the expected pressure using a measured temperature of the flow of breathable gas.

Example 81. The respiratory apparatus of any one of Examples 78-80, wherein the processor determines the accuracy of the pressure sensor by comparing a difference between the expected pressure and the measured pressure with a predetermined threshold.

Example 82. The respiratory apparatus of Example 81, wherein the predetermined threshold is 5 cmH2O.

Example 83. The respiratory apparatus of any one of Examples 81-82, wherein the processor determines the pressure sensor inaccurate when the difference exceeds the predetermined threshold.

Example 84. The respiratory apparatus of any one of Examples 81-83, wherein the processor determines the pressure sensor accurate when the difference is within the predetermined threshold.

Example 85. The respiratory apparatus of any one of Examples 78-84, wherein the processor reads measurement of the pressure from the pressure sensor, calculates the expected pressure, and compares the expected pressure with the measured pressure at a predetermined frequency over a predetermined period time of time.

Example 86. The respiratory apparatus of Example 85, wherein the predetermined frequency is between 1 and 2 hertz.

Example 87. The respiratory apparatus of any one of Examples 85-86, wherein the predetermined period of time is 5 seconds.

Example 88. The respiratory apparatus of any one of Examples 85-87, wherein the processor determines the pressure sensor inaccurate based on a plurality of comparisons between measured pressures and expected pressures.

Example 89. The respiratory apparatus of any one of Examples 52-77, wherein the subordinate characteristic of the respiratory apparatus is a first subordinate characteristic, and wherein the processor determines the accuracy of the pressure sensor by:

calculating a second subordinate characteristic of the respiratory apparatus; and comparing the second subordinate characteristic of the respiratory apparatus with the first subordinate characteristic of the respiratory apparatus.

Example 90. The respiratory apparatus of Example 89, wherein the processor calculates the second subordinate characteristic of the respiratory apparatus using a measured flow rate of the flow of breathable gas, a measured motor speed of the flow generator, and a pressure measured by the pressure sensor.

Example 91. The respiratory apparatus of Example 90, wherein the processor calculates the second subordinate characteristic of the respiratory apparatus from a measured temperature of the flow of breathable gas.

Example 92. The respiratory apparatus of any one of Examples 89-91, wherein the processor determines the accuracy of the pressure sensor by comparing a difference between the first subordinate characteristic and the second subordinate characteristic with a predetermined threshold.

Example 93. The respiratory apparatus of Example 92, wherein the predetermined threshold is 600 feet.

Example 94. The respiratory apparatus of any one of Examples 92-93, wherein the processor determines the pressure sensor inaccurate when the difference exceeds the predetermined threshold.

Example 95. The respiratory apparatus of any one of Examples 92-94, wherein the processor determines the pressure sensor accurate when the difference is within the predetermined threshold.

Example 96. The respiratory apparatus of any one of Examples 89-95, wherein the processor is configure to read a measurement of the pressure from the pressure sensor and to calculate the second subordinate characteristic based on the measurement at a predetermined frequency over a predetermined period of time.

Example 97. The respiratory apparatus of Example 96, wherein the predetermined frequency is between 1 and 2 hertz.

Example 98. The respiratory apparatus of any one of Examples 96-97, wherein the predetermined period of time is 5 seconds.

Example 99. The respiratory apparatus of any one of Examples 96-98, wherein the processor determines the pressure sensor inaccurate when an average of the second subordinate characteristic calculated during the predetermined period of time differs from the first subordinate characteristic by an offset greater than a predetermined threshold.

Example 100. The respiratory apparatus of any one of Examples 96-99, wherein the pressure sensor is determined accurate when an average of the second subordinate characteristic calculate over the predetermined period of time differs from the first subordinate characteristic by an offset not greater than a predetermined threshold.

Example 101. The respiratory apparatus of any one of Examples 52-100, wherein the processor is further configured to set the flow generator to a motor speed based on the pressure measured by the pressure sensor, when the processor determines the pressure sensor inaccurate.

Example 102. The respiratory apparatus of Example 101, wherein the processor is further configured to maintain the motor speed under a speed limit threshold.

Example 103. The respiratory apparatus of any one of Examples 52-100, wherein the processor is further configured to determine a desired gas pressure to be generated by the flow generator, and determine a desired motor speed for the flow generator based on a predetermined association between motor speed values and pressure values.

Example 104. The method or apparatus of any one of the preceding examples wherein the subordinate characteristic is altitude.

Example 105. The method or apparatus of any one of the preceding examples wherein the subordinate characteristic is atmospheric pressure in which the apparatus is operated.

Example 106. The method or apparatus of any one of the preceding examples wherein the subordinate characteristic is density altitude.

Example 107. The method or apparatus of any one of the preceding examples wherein the subordinate characteristic is pressure altitude.

The invention claimed is:

1. A respiratory apparatus configured to provide a respiratory treatment, the respiratory apparatus comprising:

a flow generator having a blower to generate a flow of breathable gas for a patient interface at a pressure above atmospheric pressure;

a pressure sensor configured to measure the pressure;

a controller coupled to the pressure sensor and the flow generator, the controller configured to control a delivery of respiratory treatment from the flow generator in a first mode according to a pressure control loop with a signal from the pressure sensor;

the controller further configured to:

test accuracy of the pressure sensor;

upon detection that the pressure sensor is inaccurate, change control of the delivery of the respiratory treatment with the flow generator from the first mode to an operational safe mode; and thereafter control delivery of respiratory treatment according to the operational safe mode, wherein the operational safe mode comprises a pressure controlled mode using the pressure sensor detected to be inaccurate.

2. The respiratory apparatus of claim 1, wherein, in the operational safe mode, the controller is configured to:

determine a desired pressure level setting of flow generator;

set a motor speed threshold;

obtain a pressure reading from the pressure sensor; and increase a motor speed of the flow generator to a next motor speed if (i) the pressure reading does not exceed the desired pressure level and (ii) the next motor speed does not exceed a maximum motor speed.

3. The respiratory apparatus of claim 2, wherein the maximum motor speed is a motor speed corresponding to the desired pressure level.

4. The respiratory apparatus of claim 2, wherein the maximum motor speed is a motor speed corresponding to a maximum pressure level.

5. The respiratory apparatus of claim 2, wherein the controller is configured to repeatedly increase a motor speed of the flow generator to a next motor speed unless increasing the motor speed (i) causes the pressure reading to exceed the desired pressure level or (ii) causes the next motor speed to exceed the maximum motor speed.

6. The respiratory apparatus of claim 1, wherein the controller is further configured with another operational safe mode wherein the another operational safe mode is a speed controlled mode, wherein the controller is further configured to:

determine a desired pressure level setting of the flow generator;

determine a desired motor speed based on the desired pressure level; and control delivery of respiratory treatment at the desired motor speed.

7. The respiratory apparatus of claim 6 further comprising a memory containing a look up table for defining one-on-one mappings between a plurality of different motor speeds and a plurality of different pressure levels, and wherein the controller is configured to determine the desired motor speed based on the look up table.

8. The respiratory apparatus of claim 6, wherein the desired pressure level is a constant pressure value maintained throughout a session of the respiratory treatment.

9. The respiratory apparatus of claim 6, wherein the desired pressure varies throughout a session of the respiratory treatment based on one or more detected breathing conditions.

10. The respiratory apparatus of claim 1, wherein the controller is configured to test the accuracy of the pressure sensor based on based a measured pressure and an altitude of the respiratory apparatus.

11. The respiratory apparatus of claim 10, wherein the controller is configured to calculate the altitude of the respiratory apparatus as a function of (a) the pressure measured by the pressure sensor and one or both of (b1) a measured flow rate of the flow of breathable gas and (b2) a measured motor speed of the flow generator.

12. The respiratory apparatus of claim 11, wherein the controller is configured to calculate the altitude of the respiratory apparatus as a function of a measured temperature of the flow of breathable gas.

13. The respiratory apparatus of claim 11, wherein the controller is configured to test the accuracy of the pressure sensor based on an average of calculated altitudes.

14. The respiratory apparatus of claim 13, wherein the controller determines the pressure sensor is accurate when the average of calculated altitudes satisfies a threshold comparison.

15. The respiratory apparatus of claim 10, wherein the altitude of the respiratory apparatus is a first altitude, and wherein the controller is configured to test accuracy of the pressure sensor by:

calculating a second altitude of the respiratory apparatus using a measured flow rate of the flow of breathable gas, a measured motor speed of the flow generator, and the pressure measured by the pressure sensor; and comparing the second altitude of the respiratory apparatus with the first altitude of the respiratory apparatus.

16. The respiratory apparatus of claim 15, wherein the controller is configured to detect that the pressure sensor is inaccurate when a difference between the first altitude and the second altitude exceeds a predetermined threshold.

17. The respiratory apparatus of claim 16, wherein the predetermined threshold is 600 feet.

18. The respiratory apparatus of claim 15, wherein the controller is configured to read a measurement of the pressure from the pressure sensor and to calculate the second altitude based on the measurement at a predetermined frequency over a predetermined period of time.

19. The respiratory apparatus of claim 18, wherein the controller is configured to detect that the pressure sensor is inaccurate when an average of the second altitude calculated during the predetermined period of time differs from the first altitude by an offset greater than a predetermined threshold.

20. The respiratory apparatus of claim 1, wherein the controller is configured to test the accuracy of the pressure sensor by:

calculating expected pressure of the gas generated by the respiratory apparatus; and comparing the expected pressure with the pressure measured by the pressure sensor.

21. The respiratory apparatus of claim 20, wherein the controller is configured to calculate the expected pressure using an altitude of the respiratory apparatus, a measured flow rate of the flow of breathable gas, and a measured motor speed of the flow generator.

22. The respiratory apparatus of claim 21, wherein the controller is configured to calculate the expected pressure using a measured temperature of the flow of breathable gas.

23. The respiratory apparatus of claim 21, wherein the controller is configured to detect that the pressure sensor is inaccurate when a difference between the expected pressure and the pressure measured by the pressure sensor exceeds a predetermined threshold.

24. The respiratory apparatus of claim 23, wherein the predetermined threshold is 5 cmH2O.

25. The respiratory apparatus of claim 20, wherein the controller is configured to read measurement of pressure from the pressure sensor, calculate the expected pressure, and compare the expected pressure with the measured pressure at a predetermined frequency over a predetermined period time of time.

26. The respiratory apparatus of claim 25, wherein the controller is configured to detect that the pressure sensor is inaccurate based on a plurality of comparisons between measured pressures and expected pressures.

27. A control method in respiratory apparatus for a respiratory treatment comprising:

controlling settings of respiratory treatment with a flow generator in a first mode according to a pressure control loop with a signal from a pressure sensor;

testing accuracy of the pressure sensor;

upon detection that the pressure sensor is inaccurate, changing mode of operations for the respiratory treatment with the flow generator from the first mode to an operational safe mode; and thereafter controlling operations according to the operational safe mode, wherein the operational safe mode comprises a pressure controlled mode using the pressure sensor detected to be inaccurate.

28. The control method of claim 27, wherein, in the operational safe mode, the control method comprises:

determining a desired pressure level setting for the flow generator;

setting a motor speed threshold;

obtaining a pressure reading from the pressure sensor; and increasing a motor speed of the flow generator to a next motor speed if (i) the pressure reading does not exceed the desired pressure level and (ii) the next motor speed does not exceed a maximum motor speed.

29. The control method of claim 28, wherein the maximum motor speed is a motor speed corresponding to the desired pressure level.

30. The control method of claim 28, wherein the maximum motor speed is a motor speed corresponding to a maximum pressure level.

31. The control method of claim 28, wherein the control method further comprises repeatedly increasing a motor speed of the flow generator to a next motor speed unless increasing the motor speed (i) causes the pressure reading to exceed the desired pressure level or (ii) causes the next motor speed to exceed the maximum motor speed.

32. The control method of claim 27, wherein, in another operational safe mode comprising a speed controlled mode, the control method comprises:

determining a desired pressure level setting of the flow generator;

determining a desired motor speed based on the desired pressure level; and controlling delivery of respiratory treatment at the desired motor speed.

33. The control method of claim 32, wherein determining the desired motor speed is further based on a look up table defining one-on-one mappings between a plurality of different motor speeds and a plurality of different pressure levels.

34. The control method of claim 32, wherein the desired pressure level is a constant pressure value maintained throughout a session of the respiratory treatment.

35. The control method of claim 32, wherein the desired pressure varies throughout a session of the respiratory treatment based on one or more detected breathing conditions.

36. The control method of claim 27, wherein testing the accuracy of the pressure sensor is based on based a measured pressure and an altitude of the respiratory apparatus.

37. The control method of claim 36, wherein the control method further comprises calculating the altitude of the respiratory apparatus as a function of (a) the pressure measured by the pressure sensor and one or both of (b1) a measured flow rate of a flow of breathable gas and (b2) a measured motor speed of the flow generator.

38. The control method of claim 37, wherein the control method further comprises calculating the altitude of the respiratory apparatus as a function of a measured temperature of the flow of breathable gas.

39. The control method of claim 37, wherein the control method further comprises testing the accuracy of the pressure sensor based on an average of the calculated altitudes.

40. The control method of claim 39, wherein the control method further comprises determining the pressure sensor is accurate when an average of the calculated altitudes satisfies a threshold comparison.

41. The control method of claim 37, wherein the control method further comprises testing the accuracy of the pressure sensor by:

calculating expected pressure of gas generated by the respiratory apparatus; and comparing the expected pressure with the pressure measured by the pressure sensor.

42. The control method of claim 41, wherein the control method further comprises calculating the expected pressure using an altitude of the respiratory apparatus, a measured flow rate of the flow of breathable gas, and a measured motor speed of the flow generator.

43. The control method of claim 42, wherein the control method further comprises calculating the expected pressure using a measured temperature of the flow of breathable gas.

44. The control method of claim 42, wherein the control method further comprises detecting that the pressure sensor is inaccurate when a difference between the expected pressure and the pressure measured by the pressure sensor exceeds a predetermined threshold.

45. The control method of claim 44, wherein the predetermined threshold is 5 cmH2O.

46. The control method of claim 41, wherein the control method further comprises reading measurement of pressure from the pressure sensor, calculating the expected pressure, and comparing the expected pressure with the measured pressure at a predetermined frequency over a predetermined period time of time.

47. The control method of claim 46, wherein the control method further comprises detecting that the pressure sensor is inaccurate based on a plurality of comparisons between measured pressures and expected pressures.

48. The control method of claim 46, wherein the altitude of the respiratory apparatus is a first altitude, and wherein the control method further comprises testing accuracy of the pressure sensor by:

calculating a second altitude of the respiratory apparatus using a measured flow rate of the flow of breathable gas, a measured motor speed of the flow generator, and the pressure measured by the pressure sensor; and comparing the second altitude of the respiratory apparatus with the first altitude of the respiratory apparatus.

49. The control method of claim 48, wherein the control method further comprises detecting that the pressure sensor is inaccurate when a difference between the first altitude and the second altitude exceeds a predetermined threshold.

50. The control method of claim 49, wherein the predetermined threshold is 600 feet.

51. The control method of claim 48, wherein the control method further comprises reading a measurement of the pressure from the pressure sensor and calculating the second altitude based on the measurement at a predetermined frequency over a predetermined period of time.

52. The control method of claim 51, wherein the control method further comprises detecting that the pressure sensor is inaccurate when an average of the second altitude calculated during the predetermined period of time differs from the first altitude by an offset greater than a predetermined threshold.

* * * * *